(12) United States Patent
Cowe et al.

(10) Patent No.: US 12,364,420 B2
(45) Date of Patent: Jul. 22, 2025

(54) LANCING DEVICE

(71) Applicant: Owen Mumford Limited, Woodstock (GB)

(72) Inventors: Toby Cowe, Woodstock (GB); Daniel Taiwo, Woodstock (GB); Anna Coe, Didcot (GB)

(73) Assignee: Owen Mumford Limited, Oxfordshire (GB)

( * ) Notice: Subject to any disclaimer, the term of this patent is extended or adjusted under 35 U.S.C. 154(b) by 897 days.

(21) Appl. No.: 17/615,157

(22) PCT Filed: Jun. 5, 2020

(86) PCT No.: PCT/EP2020/065752
§ 371 (c)(1),
(2) Date: Nov. 30, 2021

(87) PCT Pub. No.: WO2020/245445
PCT Pub. Date: Dec. 10, 2020

(65) Prior Publication Data
US 2022/0233118 A1    Jul. 28, 2022

(30) Foreign Application Priority Data

Jun. 5, 2019 (GB) .................... 1908015
Jun. 5, 2019 (GB) .................... 1908017
(Continued)

(51) Int. Cl.
*A61B 5/15* (2006.01)
*A61B 5/151* (2006.01)

(52) U.S. Cl.
CPC .. *A61B 5/150022* (2013.01); *A61B 5/150114* (2013.01); *A61B 5/150412* (2013.01);
(Continued)

(58) Field of Classification Search
CPC ........ A61B 5/150022; A61B 5/150114; A61B 5/150412; A61B 5/150916;
(Continued)

(56) References Cited

U.S. PATENT DOCUMENTS 5,324,303 A    6/1994 Strong et al.
2003/0050655 A1    3/2003 Roe
(Continued)

FOREIGN PATENT DOCUMENTS

CN    201806710 U    4/2011
GB    2521150 A    6/2015
(Continued)

OTHER PUBLICATIONS

International Preliminary Report on Patentability for corresponding PCT Application No. PCT/EP2020/065752 dated Dec. 7, 2021 (10 pages).
(Continued)

*Primary Examiner* — Michael R Bloch
*Assistant Examiner* — Nidhi N Patel
(74) *Attorney, Agent, or Firm* — QUARLES & BRADY LLP

(57) ABSTRACT

Pen-type lancing device of the re-usable type wherein a lancet body having a needle/tip is inserted; standard spring type actuator (urging member); skin touching forward face having a textured surface for pain relieve; sleeve having internal stop(s) so that the lancet does not overshoot. Also a pen-type lancing device of the re-usable type wherein a lancet body having a needle/tip is inserted; elastomer type urging member for driving the lancet; triggering means (denoted "actuating means"). Further a pen-type lancing device of the reusable type wherein a lancet body having a needle/tip is inserted; standard spring type actuator (urging member) for driving the lancet; alignment splines and coop-
(Continued)

erating alignment portion(s) for guiding the lancet movement. Even further a method of assembling a blood sampling device in which it does not matter what rotational orientation the components are assembled in.

13 Claims, 15 Drawing Sheets

(30) Foreign Application Priority Data

Jun. 5, 2019 (GB) ...................................... 1908022
Jun. 5, 2019 (GB) ...................................... 1908034

(52) U.S. Cl.
CPC .... *A61B 5/150916* (2013.01); *A61B 5/15109* (2013.01); *A61B 5/15144* (2013.01); *A61B 2560/00* (2013.01)

(58) Field of Classification Search
CPC ............ A61B 5/15109; A61B 5/15144; A61B 5/15111; A61B 5/15117; A61B 5/1513; A61B 5/150259; A61B 5/150549; A61B 5/150648; A61B 5/150297; A61B 2560/00
See application file for complete search history.

(56) References Cited

U.S. PATENT DOCUMENTS

| 2004/0098010 A1 | 5/2004 | Davison et al. |
| 2007/0239188 A1 | 10/2007 | Boozer et al. |
| 2012/0203259 A1 | 8/2012 | Saeki et al. |
| 2012/0245497 A1* | 9/2012 | Nicholls .......... A61B 5/150137 601/136 |
| 2013/0066353 A1 | 3/2013 | Hong |
| 2013/0190792 A1 | 7/2013 | Hostettler et al. |
| 2013/0274781 A1 | 10/2013 | Cha et al. |
| 2014/0052024 A1 | 2/2014 | Nicholls et al. |
| 2015/0313513 A1 | 11/2015 | Marshall et al. |

FOREIGN PATENT DOCUMENTS

| WO | 0162150 A1 | 8/2001 |
| WO | 2011055150 A2 | 5/2011 |
| WO | 2011084103 A1 | 7/2011 |

OTHER PUBLICATIONS

China National Intellectual Property Administration, First Office Action, Issued Feb. 7, 2024 for corresponding Chinese Application No. 202080041715.5 [ 5 pgs].
European Patent Office, Extended European Search Report, Issued Feb. 12, 2024 for corresponding European Patent Application No. 23208829.4 [8 pgs].
International Search Report and Written Opinion of the International Searching Authority from corresponding PCT Application No. PCT/EP2020/065752 dated Nov. 12, 2020 (16 pages).

* cited by examiner

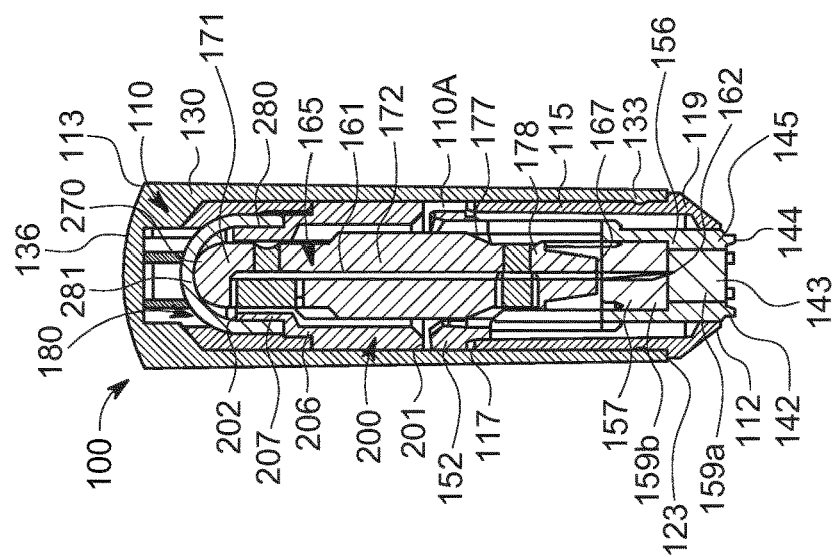
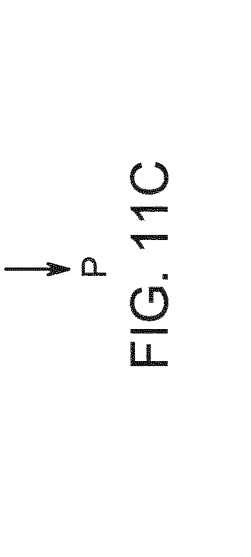
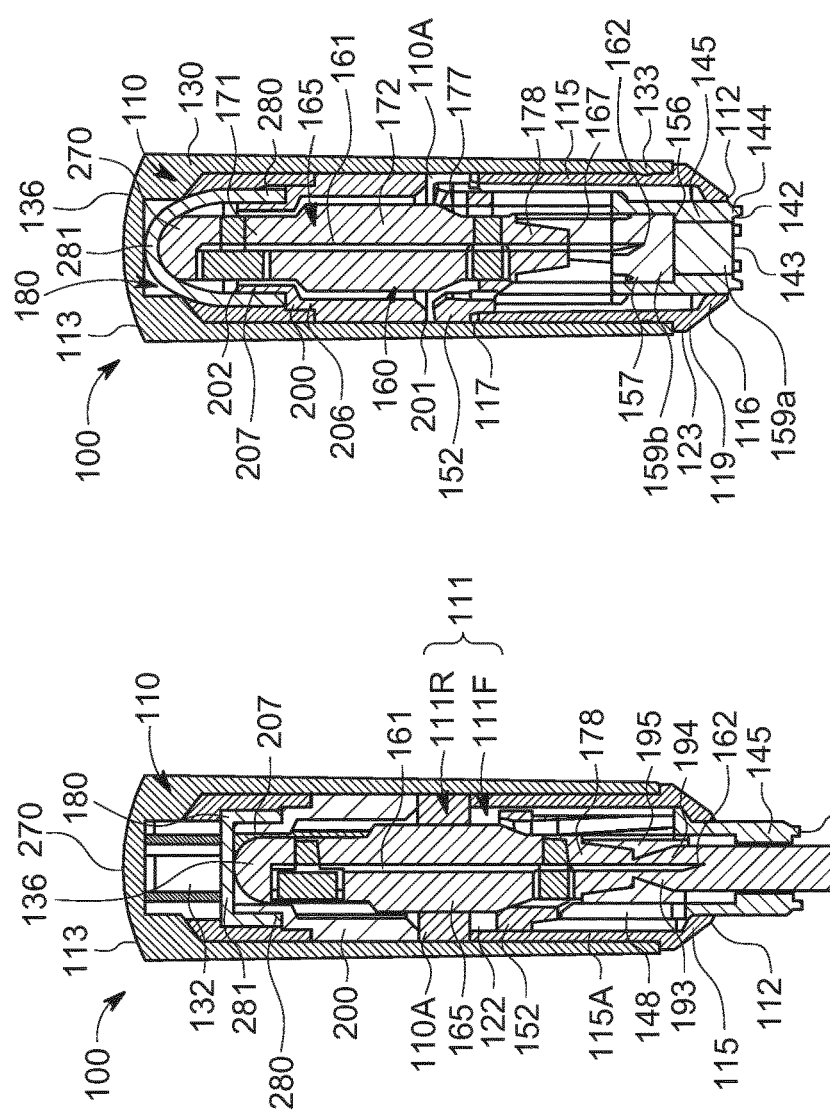
FIG. 11A
FIG. 11B
FIG. 11C

LANCING DEVICE

CROSS-REFERENCE TO RELATED APPLICATIONS

The present application represents the United States National Stage of International Application No. PCT/EP2020/065752, filed Jun. 5, 2020, which claims priority to British Patent Application Serial Nos. GB 1908015.9, filed Jun. 5, 2019; GB 1908017.5, filed Jun. 5, 2019; GB 1908022.5 filed Jun. 5, 2019; and GB 1908034.0 filed Jun. 5, 2019, and entitled, "LANCING DEVICE," each of which are incorporated herein by reference in their entirety.

TECHNICAL FIELD

The present invention relates to a lancing device. The present invention particularly relates to a lancing device that creates a skin stimulus during use and/or a lancing device that includes features which allow alignment of components of the lancing device during assembly and/or a lancing device that is activated by movement of a sleeve and/or the lancet is urged forward by an elastomeric component.

BACKGROUND ART

Blood sampling is an important part of daily routine for some people and in many cases may even be employed at home wherein the user may self-administer and/or may not be a trained medical professional. Accordingly lancing devices are commonly used to provide a simple, reliable and repeatable method of collecting blood samples. Lancing devices are used to make a small incision at a sample site on the skin (typically for example a finger tip) to draw a sample of blood. Such devices may also be referred to as capillary blood sampling devices. Single use lancing devices are used for convenience and in order to reduce risk of infection and/or cross contamination between uses.

Known blood sampling devices employ a spring or other biasing member which forces a sharp skin piercing lancet tip into the sample site following triggering of the device. For convenience and clarity, the skin piercing part of the lancet may generally be referred to herein in as a lancet "needle"; it will however be appreciated that this is non-limiting and the lancet could be formed with any suitable incision member for example a generally cylindrical needle, a sharp edge or a blade element. Typically, the lancet "needle" will be metal and the lancet will also include an injection moulded plastic lancet body.

SUMMARY OF THE INVENTION

The invention provides a lancing device comprising:
a housing having a forward end and a rearward end, the housing defining a passage having an aperture in the forward;
a lancet comprising:
  a lancet body,
  a lancet tip supported at a forward end of the lancet body so as to project from the lancet body, and
  an impact surface defined in the forward end of the lancet body at a first predetermined distance from the lancet tip;
  wherein the lancet is mounted in the passage so as to be axially moveable with respect to the housing between a first position in which the lancet tip is positioned within the housing, and a second position in which the lancet tip extends through the aperture and beyond the forward end of the housing;
an urging member which engages the lancet at least when the lancet is in the first position, and which can be energised to urge the lancet from the first position to the second position; and
a sleeve located within the housing and around the forward end of the lancet body, wherein the sleeve has a front portion that that projects through the aperture in the housing and defines an opening through which the lancet tip can project, wherein the front portion has a front surface, and
an internal stop surface located at a second predetermined distance from the front surface, wherein the internal stop surface is arranged to be engaged by the impact surface of the lancet body when in the second position, wherein the second predetermined distance is smaller than the first predetermined distance;
wherein in use, the energised urging member can move the lancet body from the first position towards the second position to cause the lancet tip to project through the opening in the sleeve by a predetermined amount before the impact surface on the lancet body engages the internal stop surface of the sleeve.

By arranging for the lancet body to impact the sleeve after the tip has pierced the skin, the front surface of the sleeve can provide an enhanced nerve stimulation so that pain perception can be reduced. The needles of hypodermic injection devices can also cause pain when inserted into the skin of a patient, and the present invention extends to such contact activated injection devices where the insertion of the needle into the skin is triggered by contact of the device with the patient body.

The sleeve can be movable between a first sleeve position in which the front portion projects a first distance from the aperture, and a second sleeve position in which the front portion projects a second distance from the aperture, wherein the second distance is less than the first distance; and the sleeve can comprise a holding structure that can be moved into and out of engagement with the lancet body, such that when the holding structure is engaged with the lancet body, movement of the sleeve from the first sleeve position to the second sleeve position moves the lancet body to the first position and energises the urging member. In this way, the device can be primed and fired by applying pressure to the skin.

Moving the holding structures out of engagement with the lancet body can release the lancet body to move to the second position under the influence of the urging member.

The diameter of the housing can be smaller at the forward end than at the rearward end. The holding structures can comprise outwardly-biased resilient legs that are held in engagement with the lancet body by the inner wall of the forward end of the housing when in the first sleeve position, and are released from engagement with the lancet body when the sleeve is moved to the second sleeve position. The engaged parts of the legs and lancet body can comprise complementary sloped surfaces. The resilient legs can comprise locking members that engage in the housing to hold the sleeve in the second sleeve position.

The resilient legs can also comprise retaining structures, wherein the retaining structures are positioned such that they will engage formations on the lancet body after recoil from the impact surface and hold it in the housing so that the lancet tip is within the housing. Alternatively, the sleeve further comprises the retaining structures.

The retaining structures can comprise inwardly biased legs. Each leg can comprise an abutment surface and the lancet body comprises a cooperating abutment surface, wherein the lancet body abutment surface abuts the leg abutment surface to prevent forward movement of the lancet in the passage. The lancet body cooperating abutment surface can be located rearwardly of the leg abutment surface when the lancet body is in the first position and wherein forward movement of the lancet body from the first position to the second position splays the leg outwardly such that the lancet body abutment surface can move past the leg abutment surface.

The front surface of the sleeve can comprise a skin contacting surface including a flat base surface and a plurality of projections extending from the flat base surface.

The urging member can comprise an elastomer or a spring.

The invention also provides a method of operating a lancing device, comprising:
- with the sleeve in the first sleeve position and the holding structure engaged with the lancet body, placing the front surface of the sleeve in contact with a skin surface;
- urging the housing towards the skin surface to move the sleeve towards the second sleeve position and move the lancet body to the first position and energise the urging member; and
- moving the holding structures out of engagement with the lancet body to releases the lancet body to move to the second position under the influence of the urging member.

In accordance with a first aspect of the present invention, there is provided a blood sampling device comprising:
(i) a housing having a forward end and a rearward end, said housing defining an aperture in said forward end and comprising an interior surface defining a passage;
(ii) an urging member mounted in said passage and comprising an elastomer;
(iii) a lancet comprising a lancet body supporting a lancet tip at a forward end thereof, said lancet being moveably mounted in said passage and arranged to move from:
  (a) a primed position in which said lancet body tensions said elastomeric portion and said lancet tip is located in said housing,
  to
  (b) a lancing position in which said lancet tip projects through said aperture in said housing;
(iv) an actuating means comprising a holding feature, the actuating means being moveable from:
  (A) a holding configuration in which said holding feature holds said lancet to prevent forward movement of said lancet to said lancing position,
  to:
  (B) a release configuration in which said holding feature does not hold said lancet;
wherein said urging member is arranged to urge said lancet forwardly in said housing from said primed position to said lancing position when said actuating means is in said release configuration.

The use of an urging member comprising an elastomer which is arranged to urge the lancet body forwardly in the housing means that metal springs, such as metal coil springs, do not have to be used. Springs are easily damaged and increase the time and costs associated with assembly due to their tendency to tangle or corkscrew together. Thus, the use of an urging member comprising an elastomeric portion reduces the complexity and costs associated with manufacture. In addition, no metal components are required in the device (other than the needle), reducing the environmental impact of the device. This is important for single use devices. To further reduce the environmental impact of the device, some or all components (other than the needle) may be formed from bio-based polymers.

The elastomer may be formed of at least one of silicone, polyurethane, neoprene, polyisoprene and/or thermoplastic elastomers. The urging member may be formed of at least one of silicone, polyurethane, neoprene, polyisoprene and/or thermoplastic elastomers. The urging member may be an elastomer.

The lancet may be moveable rearwardly in said passage from a pre-primed position in which said urging member is relaxed and said lancet tip is located in said housing to said primed position to tension said urging member, i.e. to tension said elastomer. The actuating means is in a holding configuration in the pre-primed position. The actuating means can be in a holding configuration during rearward movement of the actuating member in said passage such that it moves said lancet rearwardly in said passage from said pre-primed position to said primed position. The holding feature may be arranged to move said lancet into said primed position. The holding feature may be arranged to contact said lancet to move it into said primed position. Having a pre-primed position in which said elastomeric portion is relaxed is beneficial because it means that the device does not have to have stored energy. This also means that the blood sampling device may be formed of bio-based materials which are not good at carrying stored kinetic energy, thus improving the environmental impact of the device. In addition, storing an elastomer under tension for a long period of time may impact its performance when used. Providing a pre-primed position in which said elastomeric portion is relaxed obviates this problem as there is no stored energy.

The primed position may include a plurality of positions in which said lancet body tensions said elastomeric portion and said lancet tip is located in said housing, i.e. any position between the pre-primed position in which the elastomeric portion is relaxed and a momentary position prior to firing of the lancet when the actuating means is moving to the release configuration.

The actuating means can comprise a sleeve movably mounted in said passage and projecting through said aperture in said housing. Thus, the blood sampling device can be a contact activated blood sampling device. The blood sampling device can be a contact activated single use lancing device. The sleeve may define an aperture in a forward end thereof and when the lancet is in the lancing position, said lancet tip may project through said aperture in said sleeve.

Rearward movement of said sleeve in said passage may move said lancet rearwardly from said pre-primed position to said primed position.

The holding feature can be at least two holding arms on said sleeve, preferably three holding arms on said sleeve. The lancet body may comprise a sloped surface and each of said at least two holding arms may comprise a cooperating sloped surface arranged to contact said lancet body sloped surface when said sleeve is in said holding configuration to prevent forward movement of said lancet body in said passage. Thus, when said sleeve is in said holding configuration, for example when said lancet is in the pre-primed position and optionally during movement of said lancet from said pre-primed position to said primed position, the sloped surfaces on the holding arms may contact the sloped surface on the lancet body to prevent forward movement of the lancet body in the passage. When said sleeve is in said holding configuration the sloped surfaces on the holding arms may contact the sloped surface on the lancet body to prevent forward movement of the lancet body relative to said sleeve.

The sleeve can be moveable rearwardly in said housing from said holding configuration to said release configuration. This may move said lancet rearwardly in said passage from said pre-primed position to said primed position. The sleeve may comprise a skin contacting front surface and application of pressure to the skin contacting front surface may move the sleeve rearwardly in the housing from the holding configuration to the release configuration.

The passage can comprise a rearward portion and a forward portion immediately adjacent said passage rearward portion, said passage forward portion having a smaller diameter than said passage rearward portion, wherein at least one holding feature is at least partially located in said passage forward portion when said sleeve is in the holding position such that it is urged radially inwards, and rearward movement of said sleeve in said passage moves at least one holding feature radially outwards such that said sleeve is in said release configuration. The at least one holding feature may be biased radially outwards. Movement of the at least one holding feature radially outwards such that said sleeve is in said release position may be caused by the at least one holding feature being biased radially outwards and/or the lancet body urging against the at least one holding arm under the force of the urging member.

The housing may be formed of a front housing portion connected to a rear housing portion. The front housing portion may comprise an inner portion located inside said rear housing portion to form said forward portion of said passage.

The interior surface of said housing and said sleeve can comprise cooperating latching surfaces configured to prevent said sleeve moving forwardly in said passage when said sleeve is in said release configuration. The rear end of the inner portion of the front housing portion may be the latching surface on the interior surface of the housing. Thus, the front housing portion may project radially further into the passage than the rear housing portion and the latching surface of said housing may be formed by the rear end of said front housing portion. This is beneficial because it means that the device cannot be used. The sleeve is in the release configuration and cannot be moved into the holding configuration so it cannot be used to re-prime the lancet.

One of said front housing portion and said rear housing portion may comprise a detent and the other of said front housing portion and said rear housing portion may comprise at least one cooperating protrusion configured to snap fit with said detent to attach said front housing portion to said rear housing portion. Providing a front housing portion and a rear housing portion which may be snap fitted together means that all of the internal components of the blood sampling device can be inserted into one of the front housing portion and a rear housing portion along the longitudinal axis of the device, simplifying assembly.

The sleeve can be arranged to move said lancet rearwardly in said passage from said pre-primed position to said primed position. The cooperating sloped surfaces on the at least two holding arms and said lancet body may cooperate with one-another to prevent forward movement of said lancet body in said housing when said sleeve is in said holding configuration. Thus, when said sleeve is moved rearwardly in said housing, the lancet is moved rearwardly in said passage.

The urging member may have no stored energy in an initial assembled configuration. An initial assembled configuration can be the configuration in which the device is stored, i.e. the configuration the device is in before the user starts an injection. This means that bio-based materials can be used which are not good at carrying stored kinetic energy, thus improving the environmental impact of the device. In addition, storing an elastomer under tension for a long period of time would impact its performance when used so providing a device having no stored energy in an initial configuration, i.e. in which it is stored, obviates this problem.

The blood sampling device may further comprise a hollow support member and said urging member may comprise a transverse elastomeric portion supported by and covering one end of said hollow support member. The hollow support member may be a tubular support member. The transverse elastomeric portion transverses the passage. The transverse elastomeric portion is a planar radial portion in that it is planar when the elastomeric portion is relaxed. The elastomeric portion may be cup shaped, the base of the cup forming the transverse elastomeric portion. The elastomeric portion can be overmoulded onto said hollow support member. The elastomeric portion may be chemically bonded to said hollow support member.

The lancet body can comprise a domed rearward end arranged to contact said elastomeric portion when said lancet is in said primed position. This ensures that the rearward end of the lancet body does not damage the elastomeric portion. Damage to the elastomeric portion could prevent firing of the device or reduce the force with which the elastomer can urge the lancet forwardly in said housing.

The lancet body can comprise an alignment portion on an external surface thereof and said hollow support member can comprise a complementary alignment portion on an internal surface thereof, wherein one of said alignment portions comprises a plurality of alignment splines and the other of said alignment portions comprises at least one cooperating alignment member arranged to engage between at least two of said plurality of alignment splines in an initial assembled configuration to prevent relative rotation between said lancet body and said support member. If the support member is non-rotatably mounted, for example, affixed, in the passage, relative rotation between said lancet body and said passage is also prevented.

The alignment portion on an external surface of said lancet body may be a splined portion comprising a plurality of splines, and said complementary alignment portion on an internal surface of said hollow support member may be an inner splined portion comprising a plurality of splines.

The hollow support member can comprise an alignment portion on an external surface thereof and said housing can define a complementary alignment portion on said interior surface of said housing, wherein one of said alignment portions can comprise a plurality of alignment splines and the other of said alignment portions can comprise at least one cooperating alignment member arranged to engage between at least two of said plurality of alignment splines in an initial assembled configuration to prevent relative rotation between said hollow support member and said passage. If relative rotation between said lancet body and said support member is prevented and relative rotation between said hollow support member and said passage is prevented, relative rotation between said lancet body and said passage is prevented.

The alignment portion on an external surface of said hollow support member may be a splined portion comprising a plurality of splines, and said complementary alignment portion on said interior surface of said housing may be a splined portion comprising a plurality of splines.

The complimentary alignment portion on said interior surface of said housing may comprise a plurality of splines and each spline may comprise a flange arranged to provide a seat for said transverse elastomeric portion. The elastomeric portion may form a friction fit between the complimentary alignment portion and the hollow support member. This means that no adhesive is required to affix the elastomeric portion in the passage. The elastomeric portion may block the passage between the splines in the complimentary alignment portion on said interior surface of said housing.

Alternatively, the lancet body can comprise an alignment portion on an external surface thereof and said housing can define a complementary alignment portion on said interior surface of said housing, wherein one of said alignment portions can comprise a plurality of alignment splines and the other of said alignment portions can comprise at least one cooperating alignment member arranged to engage between at least two of said plurality of alignment splines in an initial assembled configuration to prevent relative rotation between said lancet body and said passage.

The alignment portion on an external surface of said lancet body may be a splined portion comprising a plurality of splines, and said complementary alignment portion on said interior surface of said housing may be a splined portion comprising a plurality of splines.

At least one alignment spline can comprise a guiding surface at one end thereof configured to guide an alignment member to a position between it and a neighbouring one of said alignment splines during assembly. Each alignment spline can comprise a guiding surface at one end thereof configured to guide an alignment member to a position between it and a neighbouring one of said alignment splines during assembly. The, or each, guiding surface can be a helical guiding surface, i.e. a curved, twisted, spiral or corkscrew surface. The helical surface forms a portion of a helical turn such that it acts to guide an alignment member both longitudinally and rotationally to a position between it and a neighbouring alignment spline during assembly. By providing such a guiding surface at one end of each alignment spline, the exact orientation of respective components during assembly does not matter. Even if the alignment member does not initially align with a gap between two neighbouring alignment splines, the guiding surface will guide it to a position between it and a neighbouring one of said alignment splines during assembly. The alignment splines may be equidistantly spaced.

The at least one cooperating alignment member can be at least one alignment pin. This is a simple structure that is easily guided into the correct position during assembly.

The at least one cooperating alignment member can be at least one alignment spline. An alignment spline provides a greater contact surface and therefore greater stability and structural strength than an alignment pin. The at least one cooperating alignment member may be a plurality of alignment splines. There may be the same number of alignment splines on each alignment portion.

The elastomeric portion can be arranged to span the width of said passage, i.e. the elastomeric portion can extend across the passage. The elastomeric portion may be at least one of a single piece of elastomeric material forming a continuous barrier across the passage, a mesh, a web, an elongate strip extending across the passage. Preferably, the elastomeric portion is a single continuous piece of elastomeric material traversing the passage. The elastomeric portion may block the passage.

The sleeve can comprise a skin contacting front surface and application of pressure against said skin contacting front surface can move said sleeve rearwardly in said housing from said holding configuration to said release configuration. Thus, the blood sampling device may be a contact activated blood sampling device.

The skin contacting front surface may be a textured surface. The skin contacting front surface includes a flat base surface and a plurality of projections extending/projecting from said flat base surface. The textured surface and the projections alike stimulate the skin so as to 'confuse' the nerve endings and alleviate the perceived pain experienced when the lancet tip penetrates the skin to make an incision.

In accordance with a first aspect of the present invention, there is provided a blood sampling device comprising:
(i) a housing having a forward end and a rearward end, said housing defining an aperture in said forward end and comprising an interior surface defining a passage;
(ii) a sleeve movably mounted in said passage and projecting through said aperture in said housing, said sleeve comprising at least one holding feature and at least one blocking feature;
(iii) a lancet comprising a lancet body supporting a lancet tip at a forward end thereof, said lancet being moveably mounted in said passage and moveable from:
(a) a primed position in which said lancet tip is located in said housing,
to:
(b) a lancing position in which said lancet tip projects through said aperture in said housing,
to:
(c) a safe position in which said lancet tip is located in said housing and said blocking feature blocks forward movement of said lancet in said passage,
wherein said sleeve is moveable from:
(A) a holding configuration in which said at least one holding feature holds said lancet to prevent forward movement of said lancet to said lancing position,
to:
(B) a release configuration in which said at least one holding feature does not hold said lancet; and
(iv) an urging member configured to urge said lancet forwardly in said passage from said primed position to said lancing position when said sleeve is in said release configuration;
wherein said lancet is arranged to rebound in said passage from said lancing position to said safe position.

The lancet may be urged forwardly from said primed position to said lancing position with sufficient force to rebound off the front surface of said passage. Alternatively, said sleeve may comprise an internal abutment surface and the lancet may be urged forwardly from said primed position to said lancing position with sufficient force to rebound off the internal abutment surface of said sleeve.

The sleeve may define an aperture in a forward end thereof and when the lancet is in the lancing position, said lancet tip may project through said aperture in said sleeve.

The sleeve may be an actuator. Providing a single component which comprises both a holding member to prevent firing of the device prior to use and a blocking member which actively prevents the sharp tip from projecting out of the front of the device once injection has been completed simplifies the device. It also obviates the need for a return spring which can be difficult to handle and can therefore increase the cost of manufacture. The sleeve may be formed of a plastic material. The sleeve may be formed of a bio-based polymer. This reduces the environmental impact of the device.

The at least one holding feature can be at least two holding arms, preferably three holding arms.

The lancet body may comprise a sloped surface and each of said at least two holding arms may comprise a cooperating sloped surface arranged to contact said lancet body sloped surface when said sleeve is in said holding configuration to prevent forward movement of said lancet body in said passage. This prevents the lancet from moving to said lancing position before the device is actuated by the user. Thus, when said sleeve is in said holding configuration, for example when said lancet is in the pre-primed position and optionally during movement of said lancet from said pre-primed position to said primed position, the sloped surfaces on the holding arms may contact the sloped surface on the lancet body to prevent forward movement of the lancet body in the passage. When said sleeve is in said holding configuration the sloped surfaces on the holding arms may contact the sloped surface on the lancet body to prevent forward movement of the lancet body relative to said sleeve.

The lancet body sloped surface may be a chamfered surface. The cooperating sloped surfaces on each of the holding arms may be chamfered surfaces.

The at least one blocking feature may be at least one blocking leg i.e. an elongate member, preferably three blocking legs. The, or each, blocking leg may be located within a holding arm. The, or each, blocking leg may be located circumferentially within a holding arm. Each holding arm may comprise two fingers defining a gap therebetween and the, or each, blocking leg may be located within a gap defined between the two fingers in a holding arm. There may be only one blocking leg located within each blocking arm. The sleeve may comprise three blocking legs and three holding arms, each blocking leg being located within a separate holding arm.

The, or each, blocking leg can be resiliently deformable. Movement of said lancet from said primed position to said lancing position can deflect the or each blocking leg radially outwardly i.e. splay the or each blocking leg so that the lancet can move forwardly past it or them. The force provided by the urging member may be sufficient to splay the or each blocking leg outwardly.

The or each blocking leg may comprise an abutment surface and said lancet body may comprise a cooperating abutment surface, wherein said lancet body abutment surface abuts said at least one blocking leg abutment surface when said lancet is in said safe position to prevent forward movement of said lancet in said passage. This keeps the lancet in the safe position and reduces the chance of accidental needle stick injuries. Rearward movement of said lancet from said lancing position to said safe position can move said lancet body abutment surface rearwardly past said at least one blocking leg abutment surface.

The lancet body abutment surface and said at least one blocking leg abutment surface can be complementary sloped surfaces. The lancet body abutment surface and said at least one blocking leg abutment surface may be chamfered surfaces.

The lancet body sloped surface may also be the lancet body cooperating abutment surface. The lancet body may comprise an annular projection having a forwardly sloping front surface which forms said lancet body sloped surface and said lancet body abutment surface.

The lancet body cooperating abutment surface can be located rearwardly of said at least one blocking leg abutment surface when said lancet is in said primed position, and forward movement of said lancet body from said primed position to said lancing position can splay said at least one blocking leg outwardly such that said lancet body abutment surface moves past said at least one blocking leg abutment surface. This is because the force provided by the urging member for forward movement of said lancet from said primed position to said lancing position is sufficient to splay the at least one blocking leg. When the lancet moves to the safe position the blocking leg abutment surface moves into blocking alignment with the lancet body abutment surface. The lancet does not have sufficient energy to splay the at least one blocking leg when it is in the safe position.

The sleeve can comprise a skin contacting front surface and application of pressure against said skin contacting front surface may move said sleeve rearwardly in said housing from said holding configuration to said release configuration. Thus, the blood sampling device may be a contact activated lancing device. Said skin contacting front surface can be a textured surface. The skin contacting front surface can include a flat base surface and a plurality of projections projecting/extending forward from said flat base surface. The textured surface such as the projections are designed to stimulate the skin so as to 'confuse' the nerve endings and alleviate the perceived pain experienced when the lancet tip penetrates the skin to make an incision. This effect is exaggerated for a contact activated lancing device.

The sleeve can be moveable rearwardly in said housing from said holding configuration to said release configuration. Rearward movement of said sleeve in said passage can move said lancet rearwardly from a pre-primed position in which said urging member is relaxed and said lancet tip is located in said housing to said primed position in which said urging member is primed and said lancet tip is located in said housing. The actuating means is in a holding configuration when the lancet is in the pre-primed position. The actuating means may be in a holding configuration during rearward movement of said sleeve in said passage to move said lancet rearwardly from said pre-primed position to said primed position. This therefore prevents the lancet from moving forwardly to said lancing position. The at least one holding feature may be arranged to move said lancet into said primed position. The at least one holding feature may be arranged to contact said lancet to move it into said primed position. Having a pre-primed position in which said urging member is relaxed is beneficial because it means that the device does not have to have stored energy. This also means that the blood sampling device may be formed of bio-based materials which are not good at carrying stored kinetic energy, thus improving the environmental impact of the device.

The primed position may include a plurality of positions in which said lancet body tensions said elastomeric portion and said lancet tip is located in said housing, i.e. any position between the pre-primed position in which the elastomeric portion is relaxed and a momentary position prior to firing of the lancet when the actuating means is moving to the release configuration.

The passage may comprise a rearward portion and a forward portion immediately adjacent said passage rearward portion, said passage forward portion having a smaller diameter than said passage rearward portion, wherein at least one holding feature is at least partially located in said passage forward portion when said sleeve is in the holding position such that it is urged radially inwards, and rearward movement of said sleeve in said passage moves at least one holding feature radially outwards such that said sleeve is in said release configuration. The at least one holding feature may be biased radially outwards. Movement of the at least one holding feature radially outwards such that said sleeve is in said release configuration may be caused by the at least one holding feature being biased radially outwards and/or the lancet body urging against the at least one holding arm under the force of the urging member.

The housing may be formed of a front housing portion connected to a rear housing portion. The front housing portion may comprise an inner portion located inside said rear housing portion to form said forward portion of said passage.

One of said front housing portion and said rear housing portion may comprise a detent and the other of said front housing portion and said rear housing portion may comprise at least one cooperating protrusion configured to snap fit with said detent to attach said front housing portion to said rear housing portion. Providing a front housing portion and a rear housing portion which may be snap fitted together means that all of the internal components of the blood sampling device can be inserted into one of the front housing portion and a rear housing portion along the longitudinal axis of the device, thereby simplifying assembly.

The housing and said sleeve can comprise cooperating stop surfaces configured to prevent said sleeve moving forwardly in said passage when said sleeve is in said release configuration. The rear end of the front housing portion may form the engagement surface when the front housing portion comprises an inner portion located inside said rear housing portion to form said forward portion of said passage. Preventing the sleeve moving forwardly in the passage when the sleeve is in the release configuration is beneficial because it means that the device cannot be reused. As the sleeve is in the release configuration it cannot re-prime the lancet.

The urging member can comprise an elastomer. The urging member may comprise an elastomeric urging member supported by and covering one end of a hollow support member. The hollow support member may be a tubular support member. The elastomeric portion may be planar in a relaxed position and arranged to transverse the passage in use, for example, span the width of the passage. The elastomeric portion may be overmoulded onto said hollow support member. The elastomeric portion may be chemically bonded to said hollow support member.

The lancet body may comprise a domed rearward end arranged to urge at least a portion of said elastomeric portion rearwardly when said lancet is in said primed position to tension said elastomeric portion. Providing a domed rearward end ensures that the rearward end of the lancet body does not damage, for example pierce, the elastomeric portion. Damage to the elastomeric portion could prevent firing of the device or reduce the force with which the elastomer can urge the lancet forwardly in said housing.

The lancet body may define a splined portion on an external surface thereof and said hollow support member may define a complementary splined portion on an internal surface thereof, said lancet body splined portion and said support member complementary splined portion being configured to engage to prevent relative rotation between said lancet body and said support member in an initial assembled configuration. The support member may be non-rotationally mounted in said passage. The support member may be affixed in said passage. In such cases, relative rotation between the lancet body and the passage is prevented. The lancet body splined portion and/or the hollow support member complementary splined portion may comprise a plurality of splines.

The support member may define a splined portion on an external surface thereof and said housing may define a complementary splined portion on said housing interior surface, said support member splined portion and said housing complementary splined portion being configured to engage to prevent relative rotation between said support member and said passage in an initial assembled configuration. An initial assembled configuration can be the configuration in which the device is stored, i.e. the configuration the device is in before the user starts an injection. The hollow support member splined portion and/or said housing complimentary splined portion may comprise a plurality of splines.

The splined portion on said housing interior surface may comprises a plurality of splines and each spline may comprise a flange arranged to provide a seat for said elastomeric portion in an initial assembled configuration. The initial assembled configuration can be the configuration in which the device is stored, i.e. the configuration the device is in before the user starts an injection. This provides support for the elastomeric portion. The elastomeric portion may form a friction fit between the complimentary alignment portion and the hollow support member. This means that no adhesive is required to affix the elastomeric portion in the passage. The elastomeric portion may block the passage between the splines in the complimentary alignment portion on said interior surface of said housing.

Said lancet body may define a splined portion on an external surface thereof and said housing may define a complementary splined portion on said housing interior surface, said lancet body splined portion and said housing complementary splined portion being configured to engage to prevent relative rotation between said lancet body and said passage in an initial assembled configuration. The lancet body splined portion and/or said housing complimentary splined portion may comprise a plurality of splines.

At least one of said splined portions may comprise a helical guiding surface at one end of the or each spline, i.e. a curved, twisted, spiral or corkscrew surface. The helical surface forms a portion of a helical turn such that it acts to guide a spline both longitudinally and rotationally to a position between it and a neighbouring spline during assembly.

Each of said splined portions may be rotationally symmetrical, i.e. they look the same after some rotation by a partial turn. At least one of said splined portions may have rotational symmetry Order 6. All of said splined portions may have rotational symmetry Order 6. At least one of said splined portions may have rotational symmetry Order 8. All of said splined portions may have rotational symmetry Order 8. The rotational symmetry is about the longitudinal axis when the device is assembled. This eliminates the need for rotary alignment during assembly. If each of said splined portions is rotationally symmetrical and at least one of said splined portions comprises a helical guiding surface at one end of the or each spline, there is no need for any rotary alignment during assembly.

One or more of said passage, said lancet body and said support member may be rotationally symmetrical, i.e. they look the same after some rotation by a partial turn. Each of said passage, said lancet body and said support member may be rotationally symmetrical, i.e. they look the same after some rotation by a partial turn.

The device may further comprise a removable safety cap for at least partially covering said lancet tip, said removable safety cap comprising a graspable portion external to said housing and a stem substantially located within said housing i.e. within said passage. The graspable portion can comprise diametrically opposed gripping surfaces. This helps the user to grip and twist and/or pull the safe safety cap for removal. The stem can be frangibly connected to a forward surface of said lancet body and rotation of said graspable portion relative to said lancet body can break said frangible connection such that said cap can be removed from said housing. When relative rotation between the lancet body and the passage is prevented, for example, by splined engagement between components, rotation of the graspable portion of the safety cap by the user will ensure that the graspable portion rotates relative to the lancet body. This rotation will sever the frangible connection between the lancet body and the safety cap such that the safety cap can be removed from the housing. This exposes the sharp tip of the lancet so that the blood sampling device may be used.

The at least one blocking feature and said at least one holding feature can be integrally formed with said sleeve.

The blood sampling device can be a contact activated single use lancing device.

In accordance with a first aspect of the present invention, there is provided a blood sampling device comprising:
(i) a housing having a forward end and a rearward end, said housing defining an aperture in said forward end and comprising an interior surface defining a passage;
(ii) a lancet comprising a lancet body supporting a lancet tip at a forward end thereof, said lancet being moveably mounted in said passage; and
(iii) an urging member mounted in said passage and configured to urge said lancet forwardly in said passage from:
  (a) a primed position in which the lancet tip is located in said housing,
to:
  (b) a lancing position in which said lancet tip projects through said aperture in said housing;
wherein said housing defines an alignment portion in said passage and said lancet body defines a cooperating alignment portion on an external surface thereof;
wherein one of said alignment portion and said cooperating alignment portion comprises a plurality of alignment splines and the other comprises at least one cooperating alignment member arranged to engage between at least two of said alignment splines in an initial assembled configuration to limit relative rotation between said housing and said lancet body,
wherein at least one of said alignment splines comprises a guiding surface at one end thereof configured to guide a cooperating alignment member to a position between it and a neighbouring one of said alignment splines during assembly.

According to a second aspect of the present invention, there is provided a blood sampling device comprising:
(i) a housing having a forward end and a rearward end, said housing defining an aperture in said forward end and comprising an interior surface defining a passage;
(ii) a lancet comprising a lancet body supporting a lancet tip at a forward end thereof, said lancet being moveably mounted in said passage;
(iii) a hollow support member mounted in said passage; and
(iv) an urging member supported by said hollow support member in said passage and configured to urge said lancet forwardly in said passage from:
  (a) a primed position in which said lancet tip is located in said housing,
to:
  (b) a lancing position in which said lancet tip projects through said aperture in said housing;
wherein said hollow support member defines an alignment portion on an internal surface thereof and said lancet body defines a cooperating alignment portion on an external surface thereof;
wherein one of said alignment portion and said cooperating alignment portion comprises a plurality of alignment splines and the other comprises at least one cooperating alignment member arranged to engage between at least two of said alignment splines in an initial assembled configuration to limit relative rotation between said hollow support member and said lancet body,
wherein at least one of said alignment splines comprises a guiding surface at one end thereof configured to guide a cooperating alignment member to a position between it and a neighbouring one of said alignment splines during assembly.

Thus, in both the first and second aspect, the alignment portion and the cooperating alignment portion are adapted to cooperate with one another. The alignment and cooperating alignment portions can also be referred to as first and second alignment portions. Alternatively, they can be referred to as a female alignment portion (in the passage) and a male alignment portion (on an external surface of the lancet body) respectively.

Providing such an arrangement significantly improves the ease of manufacture. By providing such a guiding surface at one end of at least one alignment spline, the exact orientation of respective components during assembly does not matter. Even if the alignment member does not initially align with a gap between two neighbouring alignment splines, the guiding surface will guide it to a position between it and a neighbouring one of the alignment splines during assembly. The alignment splines can be equidistantly spaced.

Each alignment spline can comprise a guiding surface at one end thereof configured to guide an alignment member to a position between it and a neighbouring one of the alignment splines during assembly. As such, it does not matter which orientation the lancet is inserted into the housing. When the lancet body is inserted into the housing the, or each, alignment member will contact a guiding surface on an alignment spline to guide it between the alignment spline and a neighbouring one of the alignment splines. Thus, manual rotation of the respective components in not required. This is a significant benefit in an automated assembly process as no rotary alignment is required. The alignment portion comprising a plurality of alignment splines can be rotationally symmetrical. This further eliminates the need for rotary alignment.

The urging member can comprise an elastomer. The elastomer can be overmoulded onto the hollow support member. The elastomer can be chemically bonded to the tubular support member. The urging member can comprise a transverse elastomeric portion supported by and covering one end of the hollow support member. The transverse elastomeric portion can be planar in a relaxed position and arranged to transverse the passage in use, for example, span the width of the passage. The urging member can be overmoulded onto the tubular support member. The urging member can be chemically bonded to the tubular support member.

The lancet body can comprise a domed rearward end arranged to contact the transverse elastomeric portion of the urging member. The lancet body can comprise a domed rearward end arranged to urge at least a portion of the transverse elastomeric portion rearwardly when the lancet is in the primed position to tension the transverse elastomeric portion. Providing a domed rearward end ensures that the rearward end of the lancet body does not damage, for example pierce, the urging member. Damage to the urging member could prevent firing of the device or reduce the force with which the urging member can urge the lancet forwardly in the housing.

The hollow support member can be non-rotatably mounted in the passage. For example, the hollow support member can be affixed to the interior surface of the housing using an adhesive.

The housing can define an alignment portion (a female alignment portion) in the passage and the hollow support member can define a cooperating alignment portion (a male alignment portion) on an external surface thereof, wherein the alignment portion in the passage and the cooperating alignment portion on an external surface of the hollow support member are arranged to engage to prevent relative rotation between the hollow support member and the passage in the initial assembled configuration. An initial assembled configuration can be the configuration in which the device is stored, i.e. the configuration the device is in before use, i.e. before a lancing operation is commenced.

At least one of the alignment portion in the passage and the cooperating alignment portion on an external surface of the hollow support member can comprise a plurality of alignment splines and the other can comprise at least one cooperating alignment member arranged to engage between at least two of the alignment splines.

The alignment portion in the passage can comprise a plurality of alignment splines and two or more of the splines, for example three or more, for example all of the splines, can comprise a flange arranged to provide a seat for the urging member in the initial assembled configuration. The flange can be arranged to provide a seat for the urging member in the initial assembled configuration. The initial assembled configuration can be the configuration in which the device is stored, i.e. the configuration the device is in before the user starts an injection. This provides support for the urging member. The urging member can be sandwiched between the hollow support member and the seat. The urging member can comprise a circumferential portion surrounding at least a portion of the hollow support member. The circumferential portion can form a friction fit between the hollow support member and the alignment splines in the passage. This means that no adhesive is required to affix the urging member in the passage or to affix the urging member to the hollow support member. The transverse elastomeric portion can block the passage between the splines in the alignment portion in the passage.

At least one of the alignment portion in the passage and the cooperating alignment portion on an external surface of the hollow support member can be rotationally symmetrical i.e. they look the same after some rotation by a partial turn. At least one of the alignment portion in the passage and the cooperating alignment portion on an external surface of the hollow support member can have rotational symmetry Order 6, for example if it comprises 6 alignment splines. At least one of the alignment portion in the passage and the cooperating alignment portion on an external surface of the hollow support member can have rotational symmetry Order 8, for example if it comprises 8 alignment splines. The rotational symmetry is about the longitudinal axis when the device is assembled.

Both of the alignment portion in the passage and the cooperating alignment portion on an external surface of the hollow support member can be rotationally symmetrical i.e. they look the same after some rotation by a partial turn. Both of the alignment portion in the passage and the cooperating alignment portion on an external surface of the hollow support member can have rotational symmetry Order 6, for example if they both comprise 6 alignment splines. Both of the alignment portion in the passage and the cooperating alignment portion on an external surface of the hollow support member can have rotational symmetry Order 8, for example if they both comprise 8 alignment splines. The rotational symmetry is about the longitudinal axis when the device is assembled.

The, or each, guiding surface can be a helical guiding surface i.e. a curved, twisted, spiral or corkscrew surface. The helical surface forms a portion of a helical turn such that it acts to guide an alignment member both longitudinally and rotationally to a position between it and a neighbouring alignment spline during assembly.

The at least one cooperating alignment member can be at least one alignment pin. This is a simple structure that is easily guided into the correct position during assembly.

The at least one cooperating alignment member can be at least one alignment spline. An alignment spline provides a greater contact surface and therefore greater stability and structural strength than an alignment pin. The at least one cooperating alignment member can be a plurality of alignment splines. An alignment portion and its corresponding cooperating alignment portion can comprise the same number of alignment splines as each other. In some embodiments, each alignment portion and its corresponding cooperating alignment portion comprises the same number of alignment splines as each other. The alignment portion and its corresponding cooperating alignment portion therefore can have complimentary profiles.

Each alignment spline on an alignment portion can engage between two alignment splines as its corresponding cooperating alignment portion and vice versa. An alignment portion and its corresponding cooperating alignment portion can for example each comprise six alignment splines. An alignment portion and its corresponding cooperating alignment portion can each comprise eight alignment splines.

The female alignment portion and the male alignment portion can engage to prevent relative rotational movement between the lancet body and the housing. Thus, no rotational movement between the two components is possible.

Each alignment spline on at least one alignment portion or at least one cooperating alignment portion can comprise a guiding surface at one end thereof configured to guide an alignment spline or a cooperating alignment member to a position between it and a neighbouring one of the alignment splines during assembly.

An alignment portion and its corresponding cooperating alignment portion engage to prevent relative rotational movement between the lancet body and the housing or to prevent relative rotational movement between the lancet body and the hollow support member. Thus, no rotational movement between the two components is possible. For example, the alignment portion on the housing and the cooperating alignment portion on the lancet body can engage to prevent relative rotational movement between the lancet body and the housing. The alignment portion on the hollow support member and the cooperating alignment portion on the lancet body can engage to prevent relative rotational movement between the lancet body and the hollow support member. The alignment portion on the housing and the cooperating alignment portion on the support member can engage to prevent relative rotational movement between the housing and the urging member.

Both of the female alignment portion and the male alignment portion can be rotationally symmetrical, i.e. they look the same after some rotation by a partial turn. Both of the female alignment portion and the male alignment portion can have rotational symmetry Order 6. Both of the female alignment portion and the male alignment portion can have rotational symmetry Order 8. The rotational symmetry is about the longitudinal axis when the device is assembled.

At least one of the alignment portion in the passage and the cooperating alignment portion on an external surface of the lancet body can be rotationally symmetrical i.e. they look the same after some rotation by a partial turn. At least one of the alignment portion in the passage and the cooperating alignment portion on an external surface of the lancet body can have rotational symmetry Order 6, for example if it comprises 6 alignment splines. At least one of the alignment portion in the passage and the cooperating alignment portion on an external surface of the lancet body can have rotational symmetry Order 8, for example if it comprises 8 alignment splines. The rotational symmetry is about the longitudinal axis when the device is assembled.

Both of the alignment portion in the passage and the cooperating alignment portion on an external surface of the lancet body can be rotationally symmetrical i.e. they look the same after some rotation by a partial. Both of the alignment portion in the passage and the cooperating alignment portion on an external surface of the lancet body can have rotational symmetry Order 6, for example if they both comprise 6 alignment splines. Both of the alignment portion in the passage and the cooperating alignment portion on an external surface of the lancet body can have rotational symmetry Order 8, for example if they both comprise 8 alignment splines. The rotational symmetry is about the longitudinal axis when the device is assembled.

At least one of the alignment portion on an internal surface of the hollow support member and the cooperating alignment portion on an external surface of the lancet body can be rotationally symmetrical i.e. they look the same after some rotation by a partial turn. At least one of the alignment portion on an internal surface of the hollow support member and the cooperating alignment portion on an external surface of the lancet body can have rotational symmetry Order 6, for example if it comprises 6 alignment splines. At least one of the alignment portion on an internal surface of the hollow support member and the cooperating alignment portion on an external surface of the lancet body can have rotational symmetry Order 8, for example if it comprises 8 alignment splines. The rotational symmetry is about the longitudinal axis when the device is assembled.

Both of the alignment portion on an internal surface of the hollow support member and the cooperating alignment portion on an external surface of the lancet body can be rotationally symmetrical i.e. they look the same after some rotation by a partial turn. Both of the alignment portion on an internal surface of the hollow support member and the cooperating alignment portion on an external surface of the lancet body can have rotational symmetry Order 6, for example if they both comprise 6 alignment splines. Both of the alignment portion on an internal surface of the hollow support member and the cooperating alignment portion on an external surface of the lancet body can have rotational symmetry Order 8, for example if they both comprise 8 alignment splines. The rotational symmetry is about the longitudinal axis when the device is assembled.

One or more of the passage, the lancet body, the internal surface of the support member and the external surface of the support member can be rotationally symmetrical, i.e. they look the same after some rotation by a partial turn. Each of the passage, the lancet body and the support member can be rotationally symmetrical, i.e. they look the same after some rotation by a partial turn.

The device can further comprise a removable safety cap for at least partially covering the lancet tip, the removable safety cap comprising a graspable portion external to the housing and a stem substantially within the housing. The graspable portion can comprise diametrically opposed gripping surfaces. This helps the user to grip and twist and/or pull the safe safety cap for removal. The stem can be frangibly connected to a forward end, e.g. a front surface, of the lancet body and rotation of the graspable portion relative to the lancet body can break the frangible connection such that the cap can be removed from the housing. When relative rotation between the lancet body and the passage is prevented, for example, by splined engagement between components, rotation of the graspable portion of the safety cap by the user will ensure that the graspable portion rotates relative to the lancet body. This rotation will sever the frangible connection between the lancet body and the safety cap such that the safety cap can be removed from the housing. This exposes the sharp tip of the lancet so that the blood sampling device can be used. Until the safety cap is removed, the sharp tip can be hermetically sealed in the safety cap.

The blood sampling device can further comprise a sleeve movably mounted in the passage and projecting through the aperture in the housing wherein the sleeve can comprise at least one holding feature and is moveable from a holding configuration in which the at least one holding feature holds the lancet to prevent forward movement of the lancet to the lancing position to a release configuration in which the at least one holding feature does not hold the lancet. The sleeve can be rotationally symmetrical, i.e. it looks the same after some rotation by a partial turn. The sleeve can have rotational symmetry Order 3.

The at least one holding feature can be at least two holding arms, preferably three holding arms. The lancet body can comprise a sloped surface and each of the at least two holding arms can comprise a cooperating sloped surface arranged to contact the lancet body sloped surface when the sleeve is in the holding configuration to prevent forward movement of the lancet body in the passage. This prevents the lancet from moving to the lancing position before the device is actuated by the user. Thus, when the sleeve is in the holding configuration, for example when the lancet is in the pre-primed position and optionally during movement of the lancet from the pre-primed position to the primed position, the sloped surfaces on the holding arms can contact the sloped surface on the lancet body to prevent forward movement of the lancet body in the passage. When the sleeve is in the holding configuration the sloped surfaces on the holding arms can contact the sloped surface on the lancet body to prevent forward movement of the lancet body relative to the sleeve.

The lancet body sloped surface can be a chamfered surface. The cooperating sloped surfaces on each of the holding arms can be chamfered surfaces.

The sleeve can comprise a skin contacting front surface and application of pressure against the skin contacting front surface can move the sleeve rearwardly in the housing from the holding configuration to the release configuration. Thus, the sleeve can be an actuator. The blood sampling device can be a contact activated device. The blood sampling device can be a contact activated single use lancing device.

The skin contacting front surface can be a textured surface. The skin contacting front surface can include a flat base surface and a plurality of projections extending/projecting from the flat base surface. The textured surface such as the projections are designed to stimulate the skin so as to 'confuse' the nerve endings and alleviate the perceived pain experienced when the lancet tip penetrates the skin to make an incision.

Rearward movement of the sleeve in the passage can move the lancet rearwardly from a pre-primed position in which the urging member is relaxed and the lancet tip is located in the housing to the primed position in which the urging member is primed and the lancet tip is located in the housing. The actuating means is in a holding configuration in the pre-primed position. The holding feature can be arranged to move the lancet into the primed position. Having a pre-primed position in which the urging member is relaxed is beneficial because it means that the device does not have to have stored energy. This also means that the blood sampling device can be formed of biobased materials which are not good at carrying stored kinetic energy, thus improving the environmental impact of the device. Thus, one or more of the lancet body, the sleeve, the housing and the support member can be formed of a bio-based polymer. All of the lancet body, the sleeve, the housing and the support member can be formed of a bio-based polymer.

According to a third aspect of the present invention, there is provided a method of assembling a blood sampling device according to any preceding embodiments of the blood sampling device comprising the steps of:
(i) providing a front housing portion defining an aperture in a forward end (16) thereof and a rear housing portion;
(ii) inserting an urging member into one of said front housing portion or said rear housing portion;
(iii) inserting a lancet comprising a lancet body supporting a lancet tip at a forward end thereof into one of said front housing portion or said rear housing portion;
(iv) affixing said front housing portion to said rear housing portion to form a housing comprising an interior surface defining a passage with said urging member and said lancet located in said passage;
wherein said housing defines an alignment portion in said passage and said lancet body defines a cooperating alignment portion on an external surface thereof;
wherein one of said alignment portion and said cooperating alignment portion comprises a plurality of alignment splines and the other comprises at least one cooperating alignment member,
wherein at least one alignment spline comprises a guiding surface at one end thereof which guides a cooperating alignment member to a position between it and a neighbouring one of said alignment splines to limit relative rotation between said housing and said lancet body.

According to a fourth aspect of the present invention, there is provided a method of assembling a blood sampling device according to any preceding embodiments of the blood sampling device comprising the steps of:

(i) providing a front housing portion defining an aperture in a forward end (116) thereof and a rear housing portion;
(ii) inserting an urging member and a hollow support member into one of said front housing portion or said rear housing portion wherein said hollow support member supports said urging member;
(iii) inserting a lancet comprising a lancet body supporting a lancet tip at a forward end thereof into one of said front housing portion or said rear housing portion;
(iv) affixing said front housing portion to said rear housing portion to form a housing comprising an interior surface defining a passage with said hollow support member, said urging member and said lancet located in said passage;
wherein said hollow support member defines an alignment portion on an internal surface (212) thereof and said lancet body defines a cooperating alignment portion on an external surface thereof;
wherein one of said alignment portion and said cooperating alignment portion comprises a plurality of alignment splines and the other comprises at least one cooperating alignment member,
wherein at least one alignment spline comprises a guiding surface at one end thereof which guides a cooperating alignment member to a position between it and a neighbouring one of said plurality of alignment splines to limit relative rotation between said hollow support member and said lancet body.

The method can be an automated assembly process. As no rotational alignment is needed for any of the components of the blood sampling device, this provides a much more efficient automated assembly process. With regards to equipment, having free orientation on assembly (i.e. it does not matter what rotational orientation the components are assembled in) saves a significant amount of time, thus reducing cost. Furthermore, having free orientation on assembly removes one of the considerable causes of assembly failure, namely the incorrect orientation of assembly components. The below assembly process will be described as a manual process for simplicity but the same principles of orientation free assembly apply equally to an automated assembly process.

A significant portion of the cost associated with single use lancing devices is associated with the assembly of the parts. It would therefore be desirable to provide a device structure enabling simplified assembly.

Whilst the invention has been described above, it extends to any inventive combination of the features set out above, or in the following description. These and other aspects of the present invention will be apparent from the following specific description, in which embodiments of the present invention are described, by way of examples only, and with reference to the accompanying drawings, in which:

BRIEF DESCRIPTION OF THE DRAWINGS

FIG. 11(a) is a side sectional view of the blood sampling device of FIG. 1 in an initial assembled configuration;

FIG. 11(b) is a side sectional view of the blood sampling device of FIG. 1 in a pre-release configuration;

FIG. 11(c) is a side sectional view of the blood sampling device of FIG. 1 in a firing configuration;

DESCRIPTION OF EMBODIMENTS

Figure 1:
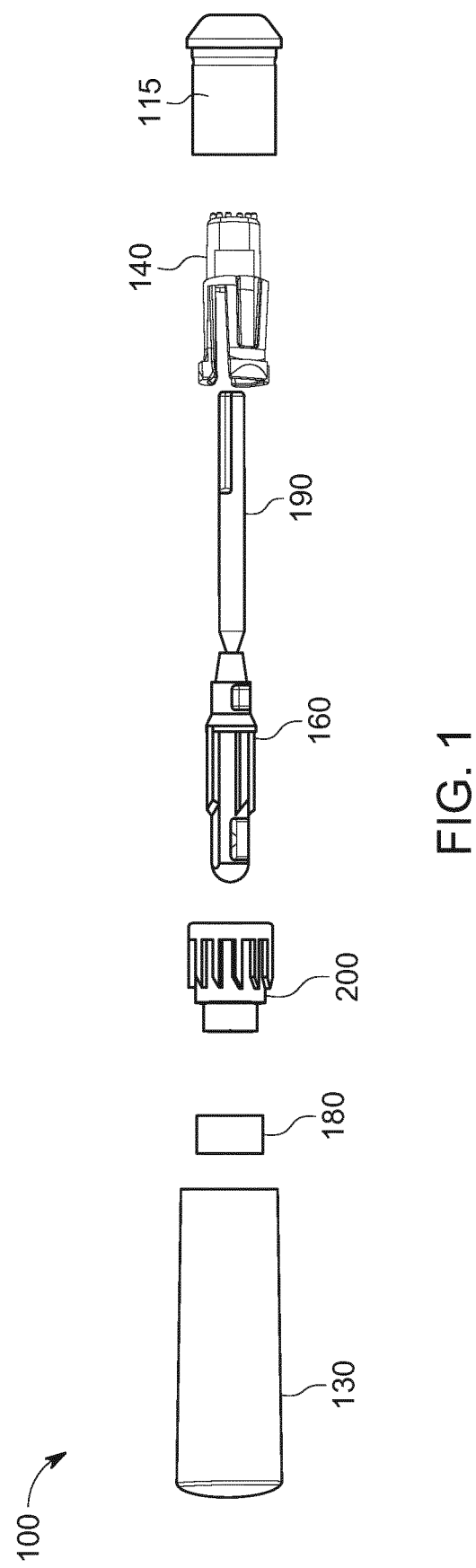
FIG. 1 is an exploded side view of a blood sampling device.

A list of reference signs used herein is given in the "Reference signs" section immediately prior to the claims.

Directional descriptors as used in the following description of the preferred embodiments of the present invention, such as "upper", "lower", "top", "bottom", "front", "rear", etc. relate to the invention when in the preferred orientation. However, it will be clear to the skilled person that the device may be in any orientation and therefore the directional descriptors would be changed accordingly.

"Front" as used herein will be understood to refer to the end of the lancing device (or components thereof) which, in use, is closest to the sample site end of the device (i.e. the end which is pointed at the skin). "Rear" as used herein will be understood to refer to the end of the lancing device (or components thereof) which, in use, is furthest from the sample end of the device (i.e. the end which is pointed away from the skin). "Forward" and "rearward" will, likewise, be understood to refer to the directions orientated towards the front and rear of the device.

The terms axial, radial and circumferential are used herein to conveniently refer to the general directions relative to the longitudinal direction of the device (or components thereof). The skilled person will, however, appreciate that these terms are not intended to be narrowly interpreted (and for example, the device may have a non-circular and/or irregular form). Typically, regardless of the specific and aesthetic design of the lancing device, the device will be generally elongate and have a longitudinal axis that is generally aligned with the lancing needle and the forward/rearward direction of travel of the lancet in use, as such, the longitudinal axis of the device will substantially coincide with (or be parallel to) the axial direction of the lancet.

Embodiment 1

Referring to FIGS. 1 to 12(d), a blood sampling device 100 includes a front housing portion 115 and a rear housing portion 130, a sleeve 140, a lancet 160 having a needle 161, a hollow support member 200 (also described as a tubular support member and a support member) and an urging member 180. The urging member 180 is an elastomer. When the blood sampling device 100 is assembled, the front housing portion 115 and the rear housing portion 130 fit together to form a housing 110 and their respective inner/interior surfaces 122, 132 together define a housing interior surface 110A defining a passage 111 in which the support member 200, urging member 180, sleeve 140 and lancet 160 are housed. Each of the components are generally concentrically arranged around the axis of the needle 161.

Figure 2:
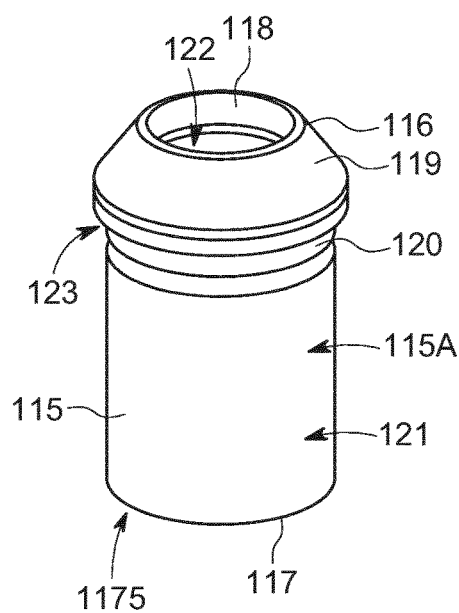
FIG. 2 is a side perspective view of the front housing portion of the blood sampling device of FIG. 1.

Referring to FIGS. 1 and 2, the front housing portion 115 is a plastic hollow cylinder having a forward end 116 and an open rearward end 117. The forward end 116 comprises a forwardly sloping bulbous head 119 defining a circular aperture 118 in the front face thereof. The bulbous head 119 projects radially outwardly from a tubular portion 124 such that a seat 123 is formed by its rear end. Spaced slightly rearwardly of the bulbous head 119 on the outer surface 121 of tubular portion 124, there is a circumferential detent 120.

Figure 3:
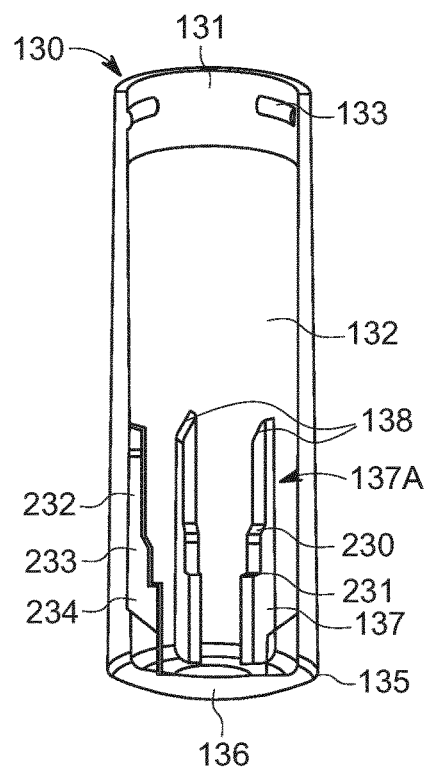
FIG. 3 is a side sectional view of the rear housing portion of the blood sampling device of FIG. 1.

Referring to FIG. 3, the rear housing portion 130 is a plastic hollow cylinder having an open forward end 131 and a closed rearward end 135 defining a convex base 136. Spaced slightly rearwardly from the open forward end 131 on the interior surface 132 of the rear housing portion 130 are three equidistantly spaced radial protrusions 133 which form a snap fit with the circumferential detent 120 on the outer surface 121 of the front housing portion 115 when the blood sampling device 100 is assembled. The interior surface 132 of the rear housing portion 130 has eight equidistantly spaced elongate ribs (i.e. splines) 137 extending from the rearward end 135 to around half way up the length of the rear housing portion 130, defining a splined portion 137A. Each elongate rib 137 has a sloped helical guiding surface 138 on the front end thereof. Each elongate rib 137 also has a curved face 230 around half way along the length of the elongate rib 137 and a flange 231 arranged to provide a seat for the urging member 180 when the blood sampling device 100 is assembled. The curved face 230 and the flange 231 divide each elongate rib 137 into three sections—a shallow forward portion 232 which is in front of the curved face 230 and has the helical guiding surface 138 at its front end; an intermediate portion 233 having an intermediate depth located between the curved face 230 and the flange 231; and a deep rearward portion 234 which is behind the flange 231 and has the largest depth, i.e. it projects radially further in to the passage 111. The eight equidistantly spaced elongate ribs (i.e. splines) 137 provide a rotationally symmetrical alignment portion on the interior surface 132 of the rear housing portion 130. The interior surface 132 of the rear housing portion 130 is rotationally symmetrical.

Figure 4:
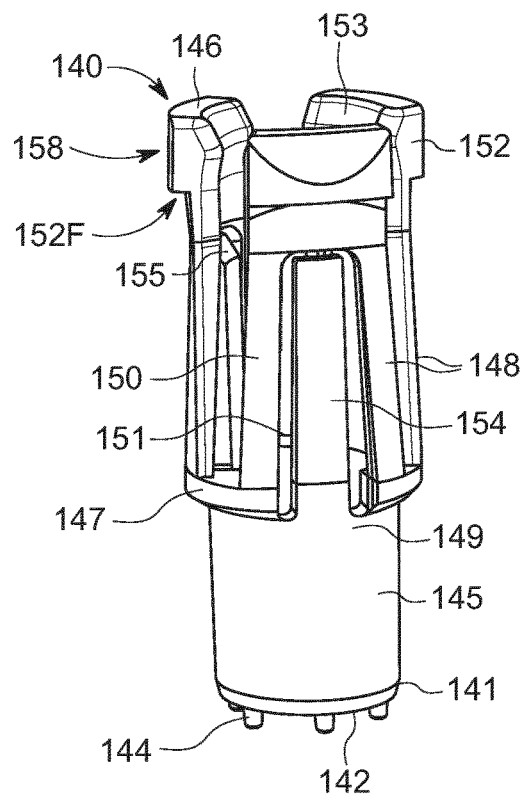
FIG. 4 is a perspective side view of the sleeve of the blood sampling device of FIG. 1 in a holding configuration.
Figure 5:
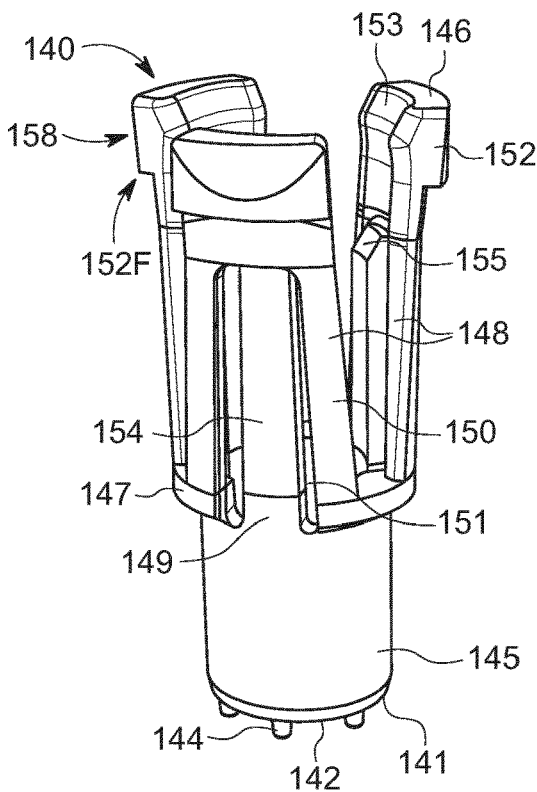
FIG. 5 is a perspective side view of the sleeve of the blood sampling device of FIG. 1 in a release configuration.

Referring to FIGS. 4 and 5, the sleeve 140 comprises a forward end 141 and a rearward end 146. The forward end 141 has a front face in the form of flat base surface 142 defining a central opening aperture 143 through which the sharp tip 162 of the lancet 160 can project in use. The flat base surface 142 also comprises a plurality of projections 144 arranged in an annular array around the central aperture 143. The projections 144 are designed to stimulate the skin so as to 'confuse' the nerve endings and alleviate the perceived pain experienced when the lancet tip penetrates the skin to make an incision.

The forward end 141 of the sleeve 140 also comprises a cylindrical tubular portion 145 extending rearwardly from the flat base surface 142 to around one third of the total length of the sleeve 140. At the rear end of the tubular portion 145 there is an annular seat 147 having the same internal diameter as the tubular portion 145 but a larger external diameter than the tubular portion 145 such that it projects radially outwardly from the rear end of the tubular portion 145. There are three equidistantly spaced gaps 149 in the annular seat 147.

Holding structures or features in the form of three holding arms 148 are equidistantly spaced around the annular seat 147 and extend rearwardly from the annular seat 147 for around two thirds of the total length of the sleeve 140, i.e. to the rearward end 146 of the sleeve 140 (i.e. about twice the length of tubular portion 145). Each holding arm 148 comprises two fingers 150 separated by a gap 151. Each gap 151 is aligned with a gap 149 in the annular seat 147. The two fingers 150 of each holding arm 148 are joined at their rearward ends such that there is no gap between them, i.e. forming a joined rearward end 158. The joined rearward end 158 of each holding arm 148 comprises a flange 152 which projects radially outwardly and a sloped surface 153 on its internal rear end surface. Each holding arm 148 is biased outwardly such that it splays outwardly in its natural resting (i.e. relaxed) position as shown in FIG. 5. This is the release configuration of the sleeve 140. The three holding arms 148 are resiliently deformable. This means that they can be pressed inwardly towards each other into a holding configuration as shown in FIG. 4 and will return to their splayed release configuration as shown in FIG. 5 on removal of this inward pressure.

Blocking features in the form of three resiliently deformable blocking or retaining legs 154 extend rearwardly from the tubular cylindrical portion 145 of the sleeve 140. Each blocking leg 154 is located in a gap 149 in the annular seat 147 and the corresponding gap 151 in a holding arm 148, i.e. each blocking leg 154 is located between the two fingers 150 of a holding arm 148. In this embodiment, all of the blocking legs 154 are longitudinally aligned with the tubular portion 145 of the sleeve 140, i.e., none of the blocking legs 154 are splayed outwardly. This means that when the sleeve 140 is in its release configuration shown in FIG. 5, the rearward end of each blocking leg 154 is positioned radially inwardly relative to the rearward end of each holding arm 148. The rear end of each blocking leg 154 has a chamfered surface in the form of abutment surface 155 on the inner rearward edge thereof.

Referring to FIGS. 11(b) to 11(e) the inner surface 157 of the tubular portion 145 of the sleeve 140 comprises a portion of reduced diameter 159a which extends rearwardly from the flat base surface 142 and an immediately adjacent portion of increased diameter 159b which extends rearwardly to the annular seat 147. The join between this portion of reduced diameter 159a and the immediately adjacent portion of increased diameter 159b forms an abutment surface 156 on the inner surface 157 of the sleeve 140.

Figure 9:
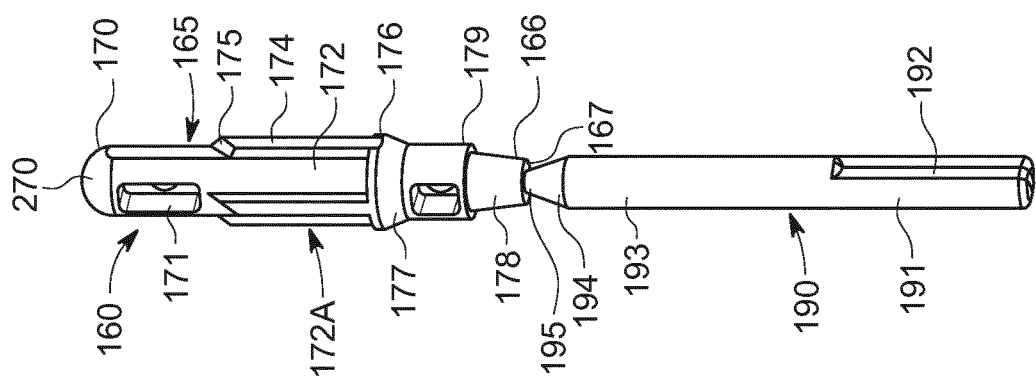
FIG. 9 is a perspective side view of the lancet and safety cap of the blood sampling device of FIG. 1 in an initial assembled configuration.

Referring to FIG. 9, the lancet 160 comprises a lancet body 165 moulded around a needle 161. The lancet body 165 has a forward end 166 and a rearward end 170. The rearward end 170 comprises a substantially cylindrical tail 171. The cylindrical tail 171 has a domed rear end 270. Immediately forward of the cylindrical tail 171 and merging with the cylindrical tail 171 is a substantially cylindrical main body portion 172 which has the same diameter as the cylindrical tail 171.

The main body portion 172 has six elongate ribs (i.e. splines) 174 equidistantly spaced around its circumference, defining a splined portion 172A. Each elongate rib/spline 174 extends axially from the rear end of the main body portion 172 to around two thirds of the length of the main body portion 172. The rearward end of each elongate rib/spline 174 has a sloped helical guiding surface 175. The forward end of each elongate rib/spline 174 merges with a circumferential protrusion 176 which projects radially outwardly on the main body portion 172. The circumferential protrusion 176 has a chamfered front face in the form of sloped surface 177. The outer surface of the main body portion 172 is rotationally symmetrical. This does not include non-functioning features such as indentations on the outer surface of the main body portion 172 which are formed by the manufacturing process.

The forward end 166 of the lancet body 165 has a frustoconical portion 178 having a planar front surface 167. The sharp tip 162 of the needle 161 projects from the front surface 167 of the lancet body 165. The front end of the frustoconical portion 178 has a smaller diameter than the rear end. The rear end of the frustoconical portion 178 has a smaller diameter than the front end of the main body portion 172 such that a front seat 179 is formed by the front end of the main body portion 172 between the circumferential edge of the main body portion 172 and the circumferential edge of the rear end of the frustoconical portion 178.

An elongate safety cap 190 is integrally moulded with the front surface 167 of the lancet body 165 such that the sharp tip 162 of the lancet needle 161 is initially concealed within the safety cap 190. The safety cap 190 comprises a graspable portion 191 which is external to the housing 110 when the blood sampling device 100 is assembled and a stem 193 which is substantially located within the housing 110 when the blood sampling device 100 is assembled. The stem 193 has a frustoconical rearward end 194 which forms a frangible connection 195 with the front surface 167 of the lancet body 160. The graspable portion 191 comprises diametrically opposed axially extending detents 192 which act as gripping surfaces for the user.

Figure 6:
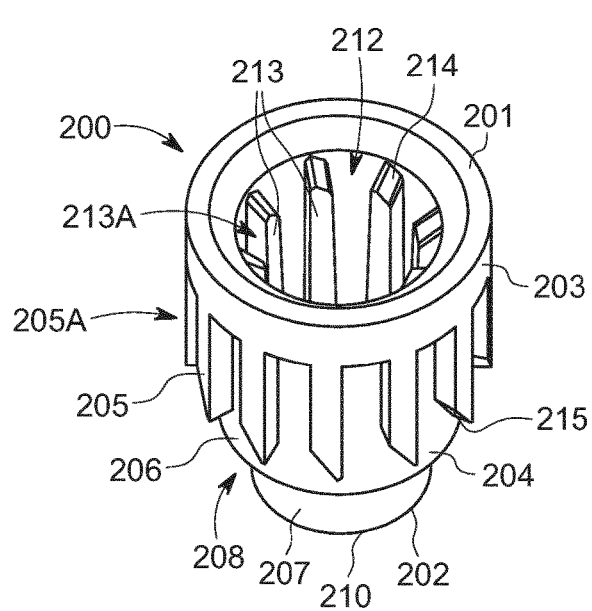
FIG. 6 is a perspective side view of the support member of the blood sampling device of FIG. 1.
Figure 7:
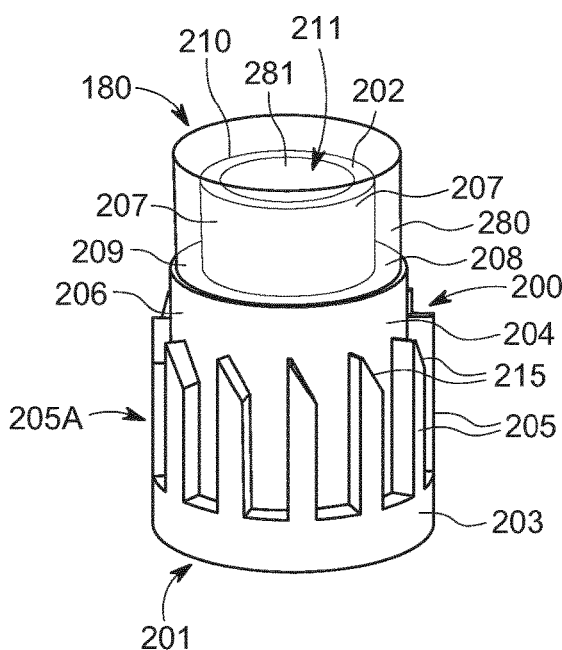
FIG. 7 is a perspective side view of the support member supporting the elastomeric urging means of the blood sampling device of FIG. 1.

Referring to FIGS. 6 and 7, the support member 200 is hollow, i.e. tubular with a generally circular cross-section. The support member 200 has a forward end 201 and a rearward end 202. It has an external stepped profile that creates three adjoining sections that decrease in diameter along its longitudinal axis from its forward end 201 to its rearward end 202.

The section at the forward end 201 is a collar 203. Extending rearwardly from the collar 203 on the external surface 204 (i.e. outer surface) of the support member 200 are a plurality of elongate ribs (i.e. splines) 205 equidistantly spaced around the circumference of the collar 203, defining a splined portion 205A. Each elongate rib 205 extends axially from the forward end of the collar 203 to around two thirds of the length of the main body section 206. The rearward end of each elongate rib 205 has a sloped helical guiding surface 215. The forward end of each elongate rib 174 merges with the collar 203.

The middle section is the main body section 206 over which the collar 203 and the elongate ribs 205 are moulded. The elongate ribs 205 therefore protrude radially outwardly from the outer surface of the main body section 206.

The section at the rearward end is a tubular support section 207. The front end of the tubular support section 207 is attached to the rear face 208 of the main body section 206. It has a smaller diameter than the main body section 206 such that the rear face 208 of the main body section 206 forms a support seat 209. The rear end 210 of the tubular support section 207 is open, i.e. it has a circular aperture 211. The outer surface of the support member 200 is rotationally symmetrical.

An elastomeric urging member 180 is provided over the tubular support section 207, i.e. it covers the tubular support section 207. The elastomeric urging member 180 is cup shaped in that it has a circumferential portion 280 which extends around the circumference of the tubular support section 207 and is supported by the support seat 209, and a transverse portion 281 which extends over the rear end 210 of the tubular support section 207. The transverse portion 281 therefore spans the width of passage 111 i.e. the diameter of the passage 111. The transverse portion is generally planar when it is not under tension from the lancet. The elastomeric urging member 180 is overmoulded onto the support member 200 in this embodiment. As such, the chemical fusion between the two components bonds them together. However, the two components could alternatively be formed separately and then attached together during assembly of the blood sampling device 100. Fusion is not required because the transverse portion 281 is sandwiched between the rear end 210 of the tubular support section 207 and the flanges 231 of the elongate ribs 137 of the housing 110 when the blood sampling device 100 is assembled. Suitable elastomeric materials have high elongation elasticity and efficient energy return. For example, silicone, polyurethane, neoprene, polyisoprene, thermoplastic elastomers could all be used as the elastomeric urging member 180.

The support member 200 also has an internal stepped profile that creates two adjoining sections corresponding to the main body section 206 and the tubular support section 207 that decrease in diameter along its longitudinal axis from its forward end 201 to its rearward end 202. A plurality of elongate ribs (i.e. splines) 213 are equidistantly spaced around the internal surface 212 (i.e. an inner surface) of the main body section 206, and define inner splined portion 213A. The elongate ribs 213 run the length of the main body section 206. The forward end of each elongate rib 213 has a sloped helical guiding surface 214.

Assembly of the blood sampling device 100 will now be described. None of the components of the blood sampling device 100 require manual rotational alignment during assembly, simplifying manufacture. In addition, none of the components require manual connection, each can simply be inserted into the housing. It is noted that the assembly of the blood sampling devices 100 may be fully automated (i.e. no manual assembly) and in large numbers. With regard to equipment, having free orientation on assembly (i.e. it does not matter what rotational orientation the components are assembled in) saves a significant amount of time, thus reducing cost. Furthermore, having free orientation on assembly removes one of the considerable causes of assembly failure, namely the incorrect orientation of assembly components. The below assembly process will be described as a manual process for simplicity but the same principles of orientation free assembly apply equally to an automated assembly process.

FIG. 11(*a*) shows the blood sampling device 100 in an initial assembled configuration. To assemble the blood sampling device 100, the front housing portion 115 is held with its forward end 116 facing downwards and its open rearward end 117 facing upwards. The sleeve 140 is inserted into the front housing portion 115 via the open rear end 117 such that the forward end 141 of the sleeve 140 projects through the circular aperture 118 in the forward end 116 of the front housing portion 115. The annular seat 147 of the sleeve 140 abuts the inner surface 122 of the forward end 116 of the front housing portion 115 which prevents further forward movement of the sleeve 140. The inner surface 122 of the front housing portion 115 has a larger diameter than the tubular cylindrical portion 145 of the sleeve 140 but a smaller diameter than the holding arms 148 when they are splayed and the sleeve 140 is in the resting configuration (FIG. 5). As such, insertion of the sleeve 140 into the front housing portion 115 forces the holding arms 148 radially inwardly so that the sleeve 140 is in the holding configuration (FIG. 4). The rotational orientation of the sleeve 140 relative to the front housing portion 115 does not matter as the inner surface 122 of the front housing portion 115 is rotationally symmetrical.

The lancet 160 and frangibly connected safety cap 190 are then inserted into the front housing portion 115 via the open rear end 117, safety cap 90 first. The diameter of the safety cap 190 is smaller than the diameter of the central aperture 143 in the flat base surface 142 of the sleeve 140 so that it passes through the central aperture 143 on insertion. The diameter of the forward end 166 of the lancet body 165 is smaller than the internal diameter of the rear end 146 of the sleeve 140, i.e. the distance between the rear ends of the holding arms 148. Therefore, the forward end 166 of the lancet body 165 passes through the rear ends of the holding arms 148 on insertion. However, the diameter of the circumferential protrusion 176 having a sloped surface 177 is larger than the diameter of the rear end 146 of the sleeve 140 when the sleeve 140 is in the holding configuration. As such, when the sloped surface 177 contacts the sloped surface 153 on the internal surfaces of the rear end of the holding arms 148, further forward movement of the lancet 160 is prevented, i.e. movement of the sloped surface 177 past the sloped surfaces 153 on the holding arms 148 is prevented. The rotational orientation of the lancet 160 and frangibly connected safety cap 190 relative to the front housing portion 115 and the sleeve 140 does not matter.

Figure 8:
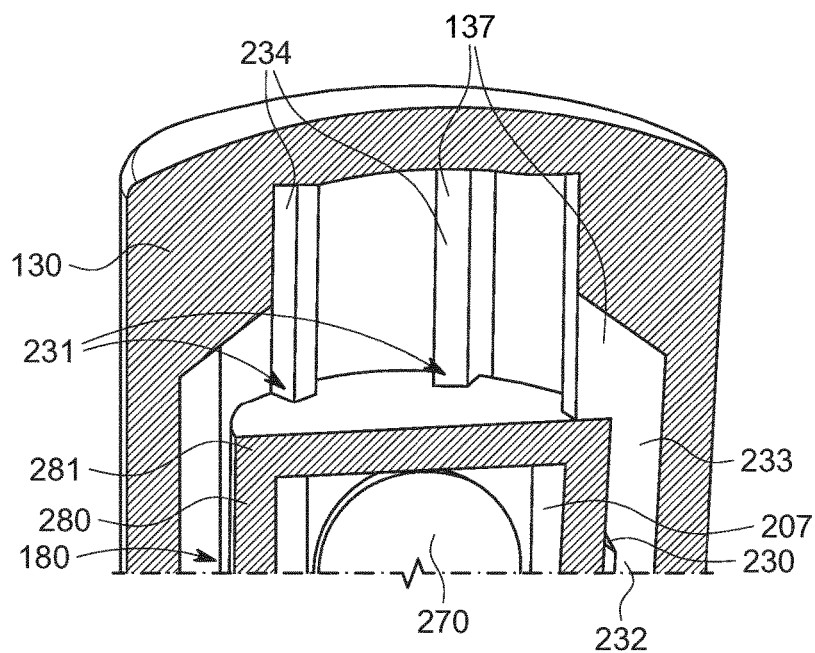
FIG. 8 is a sectional view of the rear end of the blood sampling device of FIG. 1 in an initial assembled configuration.
Figure 10:
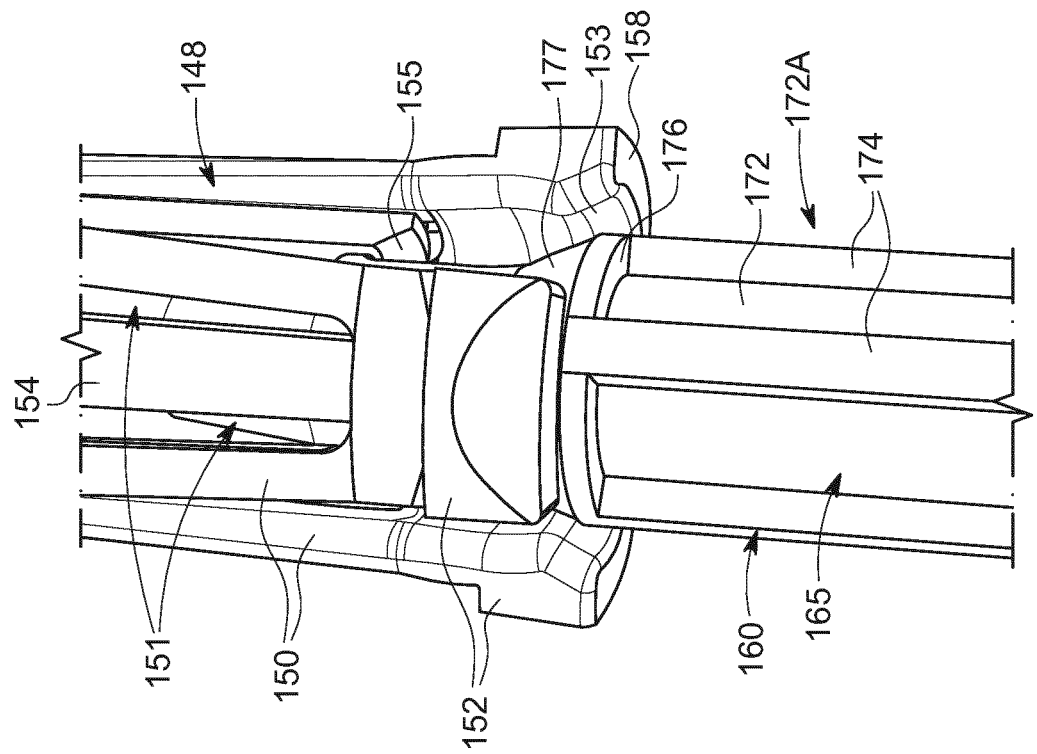
FIG. 10 is a perspective side view of the lancet and sleeve of the blood sampling device of FIG. 1 with the sleeve in a holding configuration.

Referring to FIG. 8, the rear housing portion 130 is held with its closed rearward end 135 facing downwards and its open forward end 131 facing upwards. The support member 200 and the overmoulded elastomeric urging member 180 affixed to the support member 200 are then inserted into the rear housing portion 130 via the open forward end 131. The urging member 180 and rearward end of the support member 200 are inserted first. The diameter of the circumferential portion 280 of the urging member 180 is smaller than the diametric distance between opposing elongate ribs 137 in the shallow forward portion 232, substantially the same as the diametric distance between opposing elongate ribs 137 in the intermediate portion 233 and larger than the diametric distance between opposing elongate ribs 137 in the rearward portion 234. As such, when the support member 200 and the overmoulded elastomeric urging member 180 are inserted into the rear housing portion 130, the curved faces 230 of the elongate ribs 137 guide urging member 180 such that the transverse portion 281 of the urging member 180 rests against the flanges 231 of the elongate ribs 137 and the circumferential portion 280 of the urging member 180 is located between and interacts with the intermediate portion 233 of each of the elongate ribs 137. Thus, the periphery of the transverse portion 281 of the urging member 180 is sandwiched between the flanges 231 of the elongate ribs 137 and the rear end 210 of the tubular support section 207 of the support member 200. The circumferential portion 280 is sandwiched between the tubular support section 207 of the support member 200 and the intermediate portion 233 of each of the elongate ribs 137. There is also an interference fit between the urging member 180, the tubular support section 207 of the support member 200 and the intermediate portion 233 of the rib 137.

The rotational orientation of the support member 200 relative to the rear housing portion 130 during insertion of the support member 200 and the overmoulded elastomeric urging member 180 does not matter, i.e. the support member 200 can be inserted in any orientation. If the elongate ribs 137 on the interior surface 132 of the rear housing portion 130 are not rotationally aligned with the elongate ribs 205 on the external surface 204 of the support member 200, the helical guiding surfaces 138 of the elongate ribs 137 contact the helical guiding surfaces 215 of the elongate ribs 205 so that the support member 200 self-aligns with the rear housing portion 130, i.e. no manual rotation is required from the user. Each of the elongate ribs 205 on the external surface 204 of the support member 200 is guided in between two elongate ribs 137 on the interior surface 132 of the rear housing portion 130 and vice versa by interaction of the respective helical guiding surfaces 138, 215. Therefore, the rear housing portion 130 and the support member 200 cannot rotate relative to each other when assembled.

The open forward end 131 of the rear housing portion 130, which now contains the non-rotatably engaged support member 200 and the overmoulded elastomeric urging member 180, is connected to the open rearward end 117 of the front housing portion 115 which contains the sleeve 140 and the lancet 160. The rotational orientation of the rear housing portion 130 relative to the front housing portion 115 does not matter, i.e. the rear housing portion 130 can be placed on the rear end of the front housing portion 115 in any orientation. If the elongate ribs 213 on the internal surface 212 of the support member 200 are not rotationally aligned with the elongate ribs 174 on the outer surface of the lancet body 165, then the helical guiding surfaces 214 of the elongate ribs 213 contact the helical guiding surfaces 175 of the elongate ribs 174 so that the support member 200 and thus the non-rotatably engaged rear housing portion 130 self-aligns with the lancet body 165, i.e., no manual rotation is required from the user. Each of the elongate ribs 213 on the internal surface 212 of the support member 200 is guided in between two elongate ribs 174 on the outer surface of the lancet body 165 and vice versa by the interaction between the respective helical guiding surfaces 214,175. Therefore, the support member 200 and the lancet 160 cannot rotate relative to each other when assembled. As the support member 200 and the rear housing portion 130 also cannot rotate relative to each other, none of the lancet 160, the support member 200 and the rear housing portion 130 can rotate relative to one another.

It is noted that instead of providing elongate ribs on each of the rear housing portion 130, the external surface 204 of the support member 200, the internal surface 212 of the support member 200 and the lancet body 165, any combination of splines having guiding surfaces (such as the helical guiding surfaces of this embodiment) and protrusions which can fit in between the splines could be used. Other alternative arrangements would be apparent to the skilled person.

The rear housing portion 130 is pushed forwardly over the front housing portion 115 until the three equidistantly spaced radial protrusions 133 on the interior surface 132 of the rear housing portion 130 are positioned in the circumferential detent 120 on the outer surface 121 of the front housing portion 115. The three radial protrusions 133 form a snap fit in the circumferential detent 120, securing the front housing portion 115 and the rear housing portion 130 together. The rearward end 117 of the front housing portion 115 is located within the forward end 131 of the rear housing portion 130 to form a portion of the passage 111 having a reduced diameter in the portion of overlap. The rear housing portion 130 is prevented from moving further forward by abutment of the forward end 131 of the rear housing portion 130 with the seat 123 formed by the rear end of the bulbous head 119 of the sleeve 140 and the front housing portion 115.

As such, in the initial assembled configuration, the front housing portion 115 and the rear housing portion 130 form a housing 110 having a forward end 112 and a rearward end 113. The housing 110 has an aperture 118 in said forward end 112 and the inner surface 122 of the front housing portion 115 and the interior surface 132 of the rear housing portion together form an interior surface of the housing 110 defining a passage 111. The passage 111 is narrower in the forward end 112 of the housing 110 because the front housing portion 115 is located inside the rear housing portion 130. The urging member 180, the support member 200, the lancet 160, the stem 193 of the safety cap 190 and the rearward end 146 of the sleeve 140 are located in the passage 111 in the initial assembled configuration. The forward end 141 of the sleeve 140 and the graspable portion 191 of the safety cap 190 project through the aperture 118 in the forward end 116 of the housing 110, i.e. they are not located in the passage 111 in the initial assembled configuration. The urging member 180 is relaxed, i.e. it is not under tension, in the initial assembled configuration and the domed rear end 270 of the cylindrical tail 171 of the lancet 160 is not urging the urging member 180 rearwardly. This is beneficial because it means that the elastomer does not have any stored energy in the initial assembled configuration, increasing the life of the blood sampling device 100.

The components of the blood sampling device 100 could be assembled in a different order so long as the arrangement of components in the blood sampling device 100 is the same after assembly. For example, the urging member 180 and lancet 160 with frangibly connected safety cap 190 could be inserted into the rear housing portion 130 before inserting the sleeve 140 and the front housing portion 115.

Figure 11E:
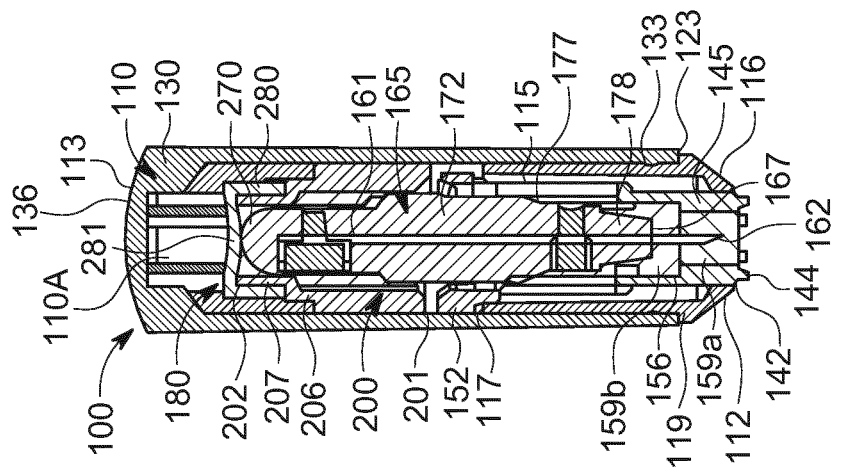
FIG. 11(e) is a side sectional view of the blood sampling device of FIG. 1 in a safe position after firing.

Referring to FIGS. 11(a)-(e) and 12(a)-(d), operation of the blood sampling device 100 will now be described. Referring to FIG. 11(a), when the blood sampling device 100 is in the initial assembled configuration, the first step to be taken by the user is removal of the safety cap 190. The safety cap 190 may be removed by holding the graspable portion 191 and twisting it relative to the housing 110 about the direction of pricking P. As each of the elongate ribs 213 on the internal surface 212 of the support member 200 is located between two elongate ribs 174 on the outer surface of the lancet body 165 and vice versa, the lancet body 165 cannot rotate relative to the support member 200. As each of the elongate ribs 205 on the external surface 204 of the support member 200 is located between two elongate ribs 137 on the interior surface 132 (i.e. inner surface) of the rear housing portion 230 and vice versa, the support member 200 cannot rotate relative to the rear housing portion 230. Thus, the lancet body 160 cannot rotate relative to the rear housing portion 130.

As such, the twisting action of the graspable portion 191 rotates the safety cap 190 relative to the housing 110 and the lancet body 165. This breaks the frangible connection 195 between the safety cap 190 and the lancet 160 such that the safety cap 190 can be removed from the housing 110. Withdrawal of the safety cap 190 in the pricking direction P exposes the sharp tip 162 of the needle 161 inside the housing 110. Thus, until this time the needle 161 is hermetically sealed prior to use. The blood sampling device is in a pre-primed position (not shown) in which the sharp tip 162 is located in the housing 110 (i.e. within the passage 111) but the urging member 180 is not yet primed. Abutment of the sloped surface 177 on the lancet body 165 with the sloped surfaces 153 on the internal surfaces of the holding arms 148 prevents the lancet 160 from moving forwardly in the passage 111 because the sleeve 140 is in the holding configuration (first sleeve position), i.e. movement of the sloped surface 177 past the sloped surfaces 153 is prevented. Abutment of the annular seat 147 of the sleeve 140 against the inner surface 122 of the forward end 116 of the front housing portion 115 prevents forward movement of the sleeve 140 in the passage 111. Thus, the blood sampling device 100 is held in the pre-primed position until actuated by the user.

To operate the blood sampling device 100, the user holds the housing 110 and places the flat base surface 142 of the sleeve 140 (which is the forwardmost part of the blood sampling device 100 in the pre-primed position) against the surface of the skin from which blood is to be sampled. The annular array of projections 144 therefore contact the skin of the user, stimulating the skin so as to 'confuse' the nerve endings and alleviate the perceived pain experienced when the lancet tip penetrates the skin to make an incision. To actuate the blood sampling device 100, the user presses the housing 110 towards the skin. This causes the housing 110 to move forwardly relative to the sleeve 140 as the sleeve 140 is held against the surface of the skin, i.e. the sleeve 140 moves rearwardly in the passage 111.

Passage 111 comprises a rearward portion 111R and a forward portion 111F immediately adjacent rearward portion 111R, forward portion 111F having a smaller diameter than rearward portion 111R. Holding arms 148 are located in passage forward portion 111F when sleeve 140 is in the holding configuration such that they are urged radially inwards, and rearward movement of sleeve 140 in passage 111 to passage rearward portion 111R results in holding arms 148 moving radially outwards such that sleeve 140 is in the release position. In certain embodiments this movement of holding arms 148 is as a result of them moving to their relaxed position. In other embodiments, this movement is as a result of sloped surface 177 of lancet body 165 (which abuts sloped surface 153 of holding arms 148) deflecting holding arms 148 radially outwards. Front housing portion 115 comprises an inner portion 115A which is located inside rear housing portion 130 to form forward portion 111F of passage 111.

Figure 12B:
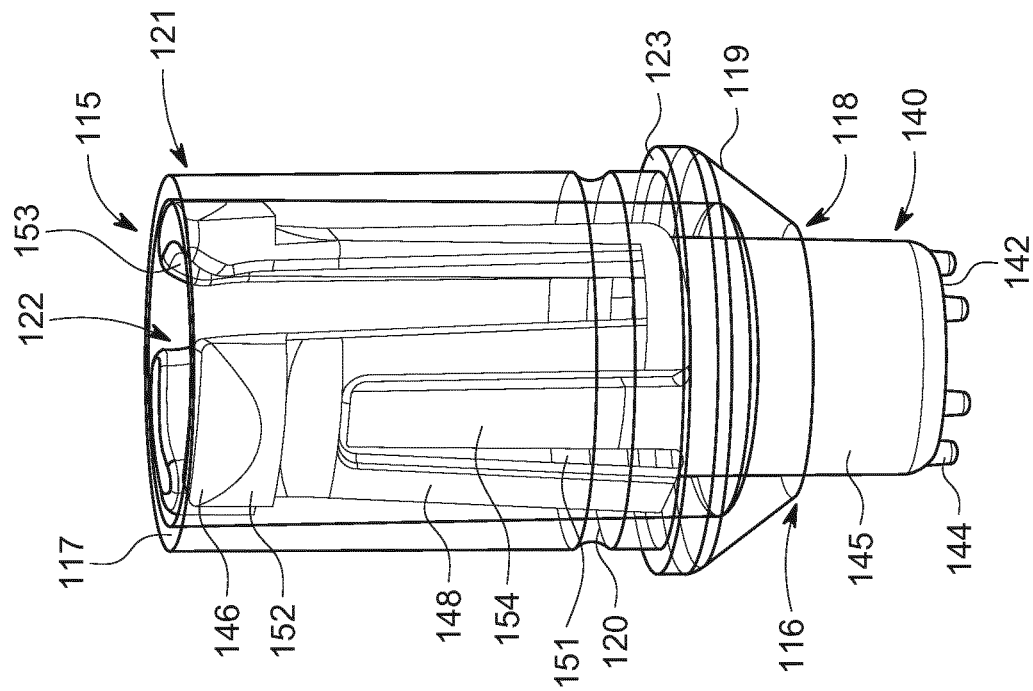
FIG. 12(b) is a part-transparent side view of the sleeve and front housing portion of the blood sampling device of FIG. 1 in a holding configuration.
Figure 12A:
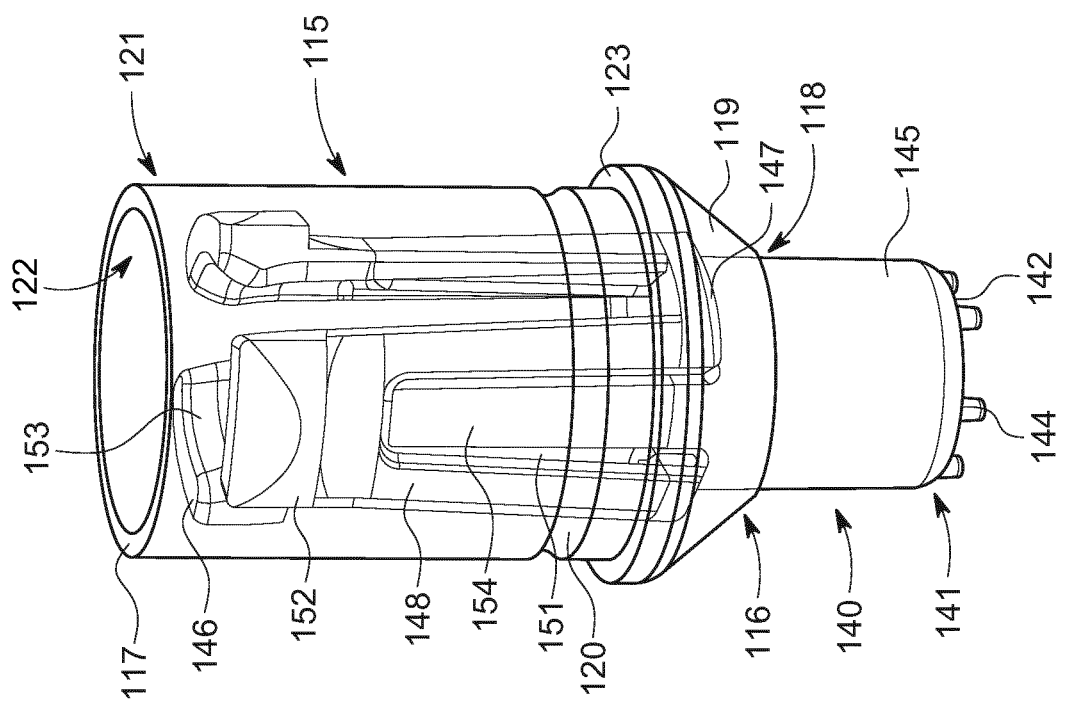
FIG. 12(a) is a part-transparent side view of the sleeve and front housing portion of the blood sampling device of FIG. 1 in an initial assembled configuration.

Referring to FIG. 12(b), the holding arms 148 are held inwardly by the front housing portion 115 during this initial rearward movement of the sleeve 140 in the passage 111 so the sleeve 140 is maintained in the holding configuration. As such, the sloped surface 177 on the lancet body 165 continues to abut the sloped surfaces 153 on the internal surfaces of the holding arms 148, preventing movement of the sloped surface 177 past the sloped surfaces 153 and thus forward movement of the lancet 160 relative to the sleeve 140. As such, the lancet 160 also moves rearwardly in the passage 111 with the sleeve 140 from the pre-primed position to a primed position. The domed rear end 270 of the cylindrical tail 171 of the lancet 160 is urging the transverse portion 281 of the urging member 180 rearwardly. As the periphery of the transverse portion 281 of the urging member 180 is sandwiched between the flanges 231 of the elongate ribs 137 in the rear housing portion 130 and the rear end 210 of the tubular support section 207 of the support member 200, the urging member 180 cannot move longitudinally in the passage 111. Thus, the transverse portion 281 of the urging member 180 is resiliently deformed rearwardly in the passage. This places the urging member 180 under tension. As the cylindrical tail 171 of the lancet 160 is domed, it does not pierce the transverse portion 281 of the urging member 180. The blood sampling device 100 is now in the pre-release configuration shown in FIG. 11(b) and the lancet 160 is in a primed position. The sharp tip 162 is located in the housing 110 (i.e. within the passage 111) in the primed position and the urging member 180 is primed, i.e., it is stretched from its resting position so that it is under tension.

If the user continues to push the blood sampling device 100 towards the skin, the sleeve 140 will continue to move rearwardly in the passage 111. Referring to FIG. 12(c), the holding arms 148 start to splay outwardly as the flange 152 of each holding arm 148 moves rearwardly past the rearward end 117 of the front housing portion 115 because the diameter of the passage 111 is larger behind the front housing portion 115. The urging member 180 which is now under tension is also urging against the domed rear end of the cylindrical tail 171 of the lancet body 165 which urges the lancet body 165 forwardly. As such, the sloped surface 177 on the lancet body 165 urges against the sloped surfaces 153 on the internal surfaces of the holding arms 148, forcing the holding arms 148 apart. However, as the front surface 152F of each flange 152 is not yet rearward of the rearward end 117 of the front housing portion 115, the holding arms 148 are still held inwardly by the front housing portion 115 and the sleeve 140 is still in the holding configuration. The lancet 160 is still in a (first) primed position because it cannot yet travel forwardly past the holding arms 148. The sharp tip 162 is located in the housing 110 (i.e. within the passage 111) in the primed position and the urging member 180 is primed, i.e., it is stretched from its resting position so that it is under tension.

Figure 12D:
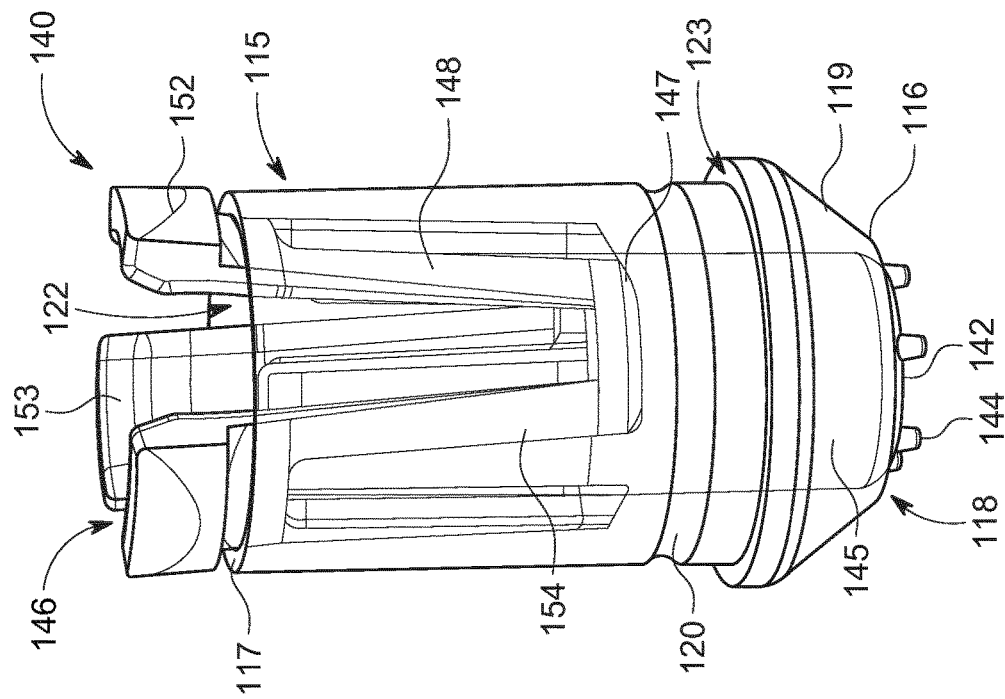
FIG. 12(d) is a part-transparent side view of the sleeve and front housing portion of the blood sampling device of FIG. 1 in a release configuration.
Figure 12C:
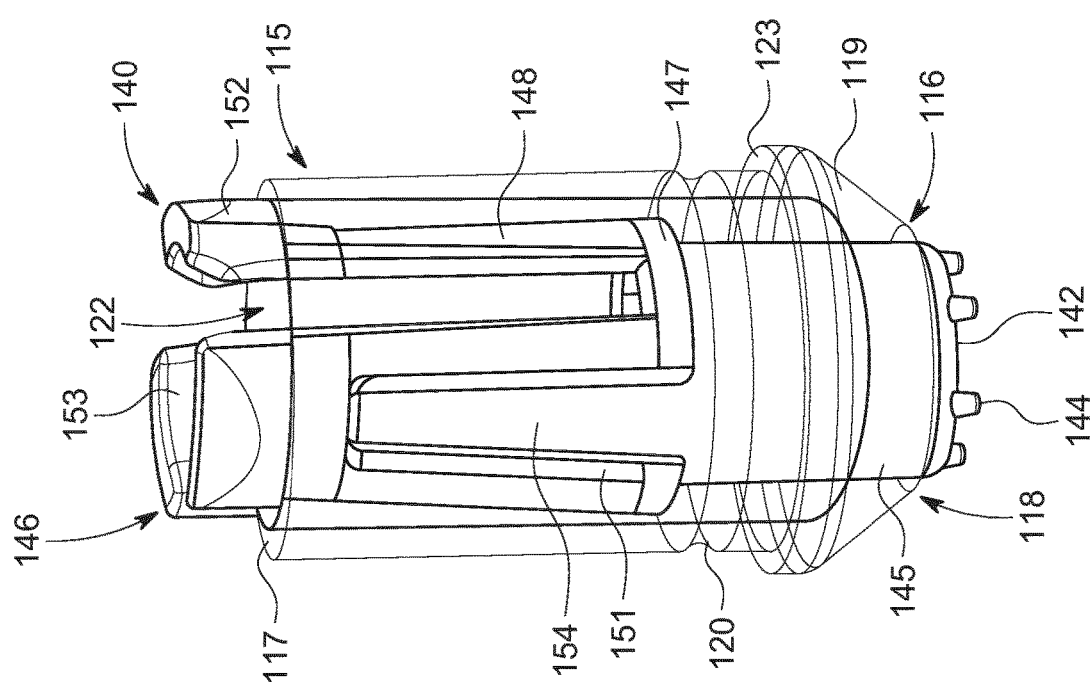
FIG. 12(c) is a part-transparent side view of the sleeve and front housing portion of the blood sampling device of FIG. 1 in a holding configuration.
Figure 13:
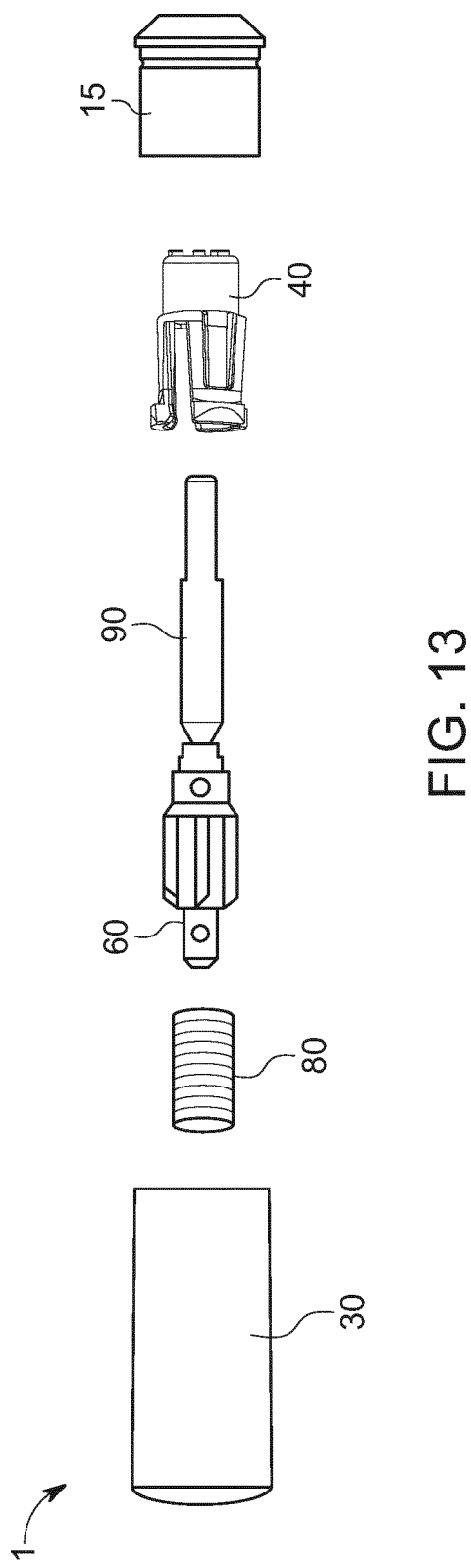
FIG. 13 is an exploded side view of a second blood sampling device.

Referring to FIG. 12(d), when the sleeve 140 moves sufficiently rearwardly in the passage 111 (second sleeve position), the flange 152 of each holding arm 148 is rearward of the rearward end 117 of the front housing portion 115. The three holding arms 148 splay outwardly under their own resilient bias and under the urging force of sloped surface 177 on the lancet body 165 against the sloped surfaces 153 on the internal surfaces of the holding arms 148. The blood sampling device 100 is in the firing configuration shown in FIG. 11(c) and the sleeve 140 is in the release configuration. This movement of the sleeve 140 from the holding configuration to the release configuration is very quick due to the sharp 90° angle between the front surface 152F of each flange 152 and the rearward end 117 of the front housing portion 115. As such, the three holding arms 148 spring outward into the release configuration as soon as the front surface 152F of each flange 152 is rearward of the rearward end 117 of the front housing portion 115, i.e. the front surface 152F of each flange 152 acts as a release point. The diameter of the circumferential protrusion 176 of the lancet body 165 is smaller than the internal diameter of the rear end 146 of the sleeve 140 when it is in the release configuration, i.e. the diameter of the circumferential protrusion 176 of the lancet body 165 is smaller than the distance between the rear ends of the holding arms 148. As such, the circumferential protrusion 176 and thus the sloped surface 177 of the lancet body 165 can move forwardly in the passage 111 past the sloped surfaces 153 and the lancet 160 fires forwardly under the force of the urging member 180.

As the lancet 160 moves forwardly in the passage 111, the sloped surface 177 of the lancet body 165 contacts the abutment surfaces 155 on the inner rearward edge of each of the three blocking legs 154. The lancet 160 cannot push the sleeve 140 forwardly in the passage 111 because the forward surface (stop surface) 152F of each flange 152 on each of the holding arms 148 abuts stop surface 117S of the rearward end 117 of the front housing portion 115, preventing forward movement of the sleeve 140, i.e. the stop surface 117S of rearward end 117 and the forward surface (stop surface) 152F act as cooperating latching surfaces. The sleeve 140 is also held in position by the user holding the blood sampling device 100 against the skin. As lancing is near instantaneous, upon reaching the release point, it would not be possible for the user to release pressure before firing of the blood sampling device 100 is finished. However, the force of the urging member 180 is sufficient for the lancet body 165 to splay the three blocking legs 154 outwardly by urging the sloped surface 177 on the lancet body 165 firstly past the abutment surfaces 155 on the inner rearward edge of each of the three blocking legs 154 and then past the inside face of each of the blocking legs 154.

Figure 11D:
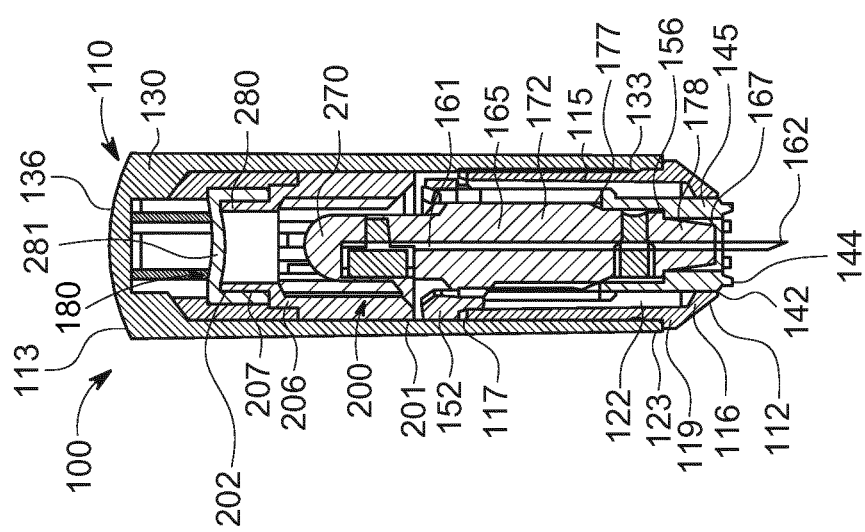
FIG. 11(d) is a side sectional view of the blood sampling device of FIG. 1 in a lancing configuration.

Referring to FIG. 11(d), the sharp tip 162 of the needle 161 projects through the central aperture 143 in the flat base surface 142 of the sleeve 140 and thus also through the aperture 118 in the forward end 116 of the housing 110, to puncture the skin of the user, drawing a sample of blood from the user. This is the lancing configuration of the blood sampling device 100 in which the lancet 160 is in a (second) lancing position. The lancet 160 continues to move forwardly in the passage 111 until the front seat impact surface 179 formed by the main body portion 172 of the lancet 160 strikes the abutment surface 156 on the inner surface 157 of the sleeve 140. The contact between the front seat and the abutment surface creates an impulse that is felt by the user as enhanced stimulation from the surface 142 and projections 144 of the sleeve 140. The relative distances between the tip 162 and the seat 179, and the abutment surface 156 and the front surface 142 of the sleeve 140 mean that the impulse arrives shortly after the tip 162 pieces the skin, the creating nerve confusion and reducing the sensation of pain.

Referring to FIG. 11(e), the front seat 179 formed by the main body portion 172 of the lancet 160 strikes the abutment surface 156 on the inner surface 157 of the sleeve 140 with sufficient force to rebound. The lancet 160 therefore travels rearwardly in the passage 111 to retract the sharp tip 162 of the needle 161 into the housing 110. This rearward movement is assisted by the blocking legs 154 returning from their outwardly splayed position to their normal position parallel to the needle axis. This ensures that the sloped surface 177 on the lancet body 160 moves rearwardly past the abutment surface 155 on the rear end of the blocking legs 154. When the front seat 179 formed by the main body portion 172 of the lancet 160 strikes the abutment surface 156 on the inner surface 157 of the sleeve 140 a significant amount of energy is lost. Therefore, there is not enough energy in the lancet 160 to re-tension the urging member 180. The urging member 180 therefore does not re-fire the lancet 160 forwardly in the passage 111 and the lancet 160 does not move forwardly with sufficient force to re-splay the blocking legs 154 and travel forwardly in the passage again. Thus, re-firing of the blood sampling device 100 is prevented and the lancet 160 is held sufficiently rearwardly from the aperture 118 in the forward end 118 in the housing 110 that the sharp tip 162 is safe. Thus, the risk of the user accidentally pricking themselves with the used lancet is significantly reduced. As discussed above, the sleeve 140 cannot move forwardly in the passage 111 because the forward surface (stop surface) 152F of the flanges 152 on each of the holding arms 148 abuts the rearward end 117 of the front housing portion 115, preventing forward movement of the sleeve 140. Therefore, the device cannot be reused.

Embodiment 2

Referring to FIGS. 13 to 22(d), a blood sampling device 1 includes a front housing portion 15 and a rear housing portion 30, a sleeve 40, a lancet 60 having a needle 61 and an urging member 80. The urging member 80 is a compression spring. When the blood sampling device 1 is assembled, the front housing portion 15 and a rear housing portion 30 fit together to form a housing 10 and their respective inner/interior surfaces 22, 32 together define a housing interior surface 10A defining a passage 11 in which the urging member 80, sleeve 40 and lancet 60 are housed. Each of the components are generally concentrically arranged around the axis of the needle 61.

Figure 14:
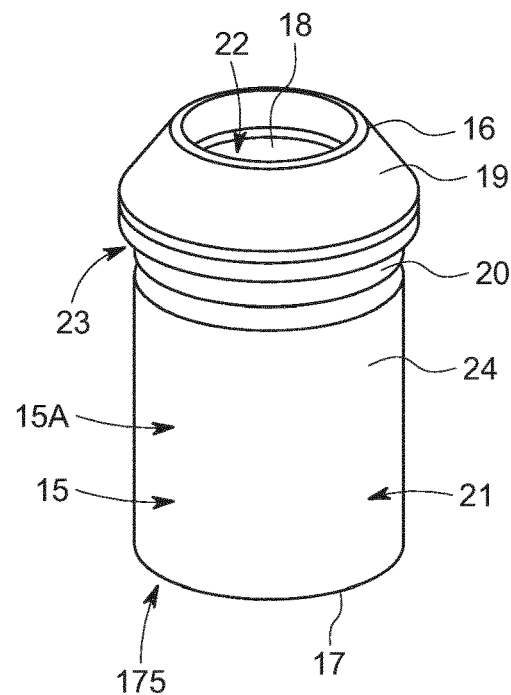
FIG. 14 is a side perspective view of the front housing portion of the blood sampling device of FIG. 13.

Referring to FIG. 14, the front housing portion 15 is a plastic hollow cylinder having a forward end 16 and an open rearward end 17. The forward end 16 comprises a forwardly sloping bulbous head 19 defining a circular aperture 18 in the front face thereof. The bulbous head 19 projects radially outwardly from a tubular portion 24 such that a seat 23 is formed by its rear end. Spaced slightly rearwardly of the bulbous head 19 on the outer surface 21 of the tubular portion 24, there is a circumferential detent 20.

Figure 15:
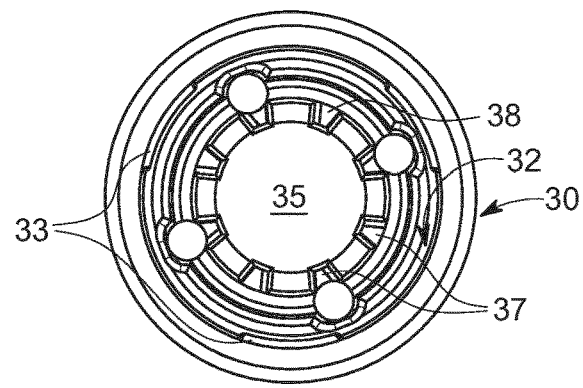
FIG. 15 is a plan view of the rear housing of the blood sampling device of FIG. 13.
Figure 16:
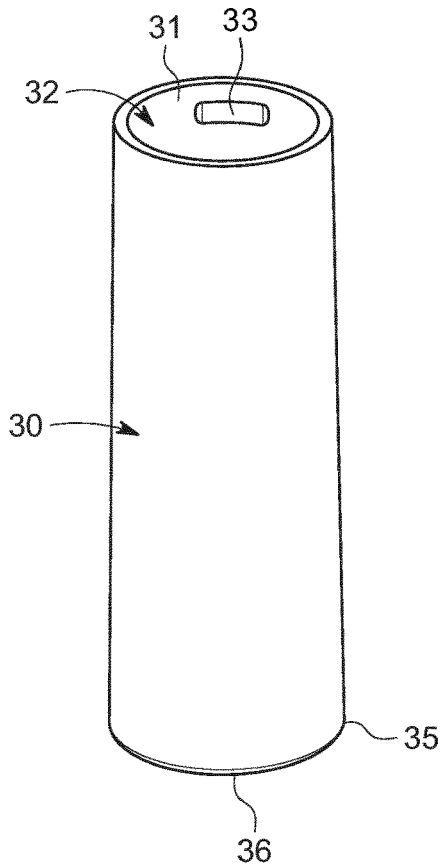
FIG. 16 is a perspective side view of the rear housing portion of the blood sampling device of FIG. 13.
Figure 17:
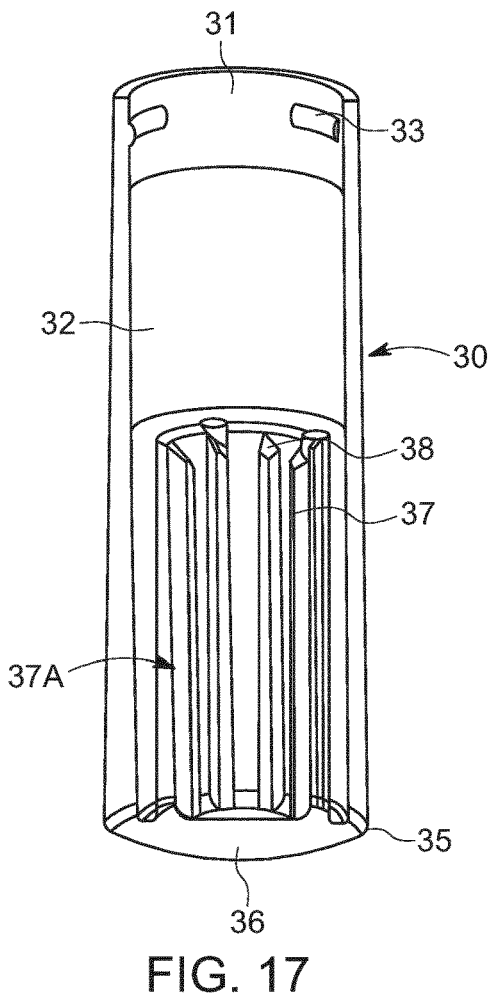
FIG. 17 is a side sectional view of the rear housing portion of the blood sampling device of FIG. 13.

Referring to FIGS. 15 to 17, the rear housing portion 30 is a plastic hollow cylinder having an open forward end 31 and a closed rearward end 35 defining a convex base 36. Spaced slightly rearwardly from the open forward end 31 on the interior surface 32 of the rear housing portion 30 are three equidistantly spaced radial protrusions 33 which form a snap fit with the circumferential detent 20 on the outer surface 21 of the front housing portion 15 when the blood sampling device 1 is assembled. The interior surface 32 of the rear housing portion 30 has eight equidistantly spaced elongate ribs (i.e. splines) 37 extending from the closed rearward end 35 to around half way up the length of the rear housing portion 30, defining a splined portion 37A. Each elongate rib 37 has a sloped helical guiding surface 38 on the front end thereof. The eight equidistantly spaced elongate ribs (i.e. splines) 37 provide a rotationally symmetrical alignment portion on the interior surface 32 of the rear housing portion 30. The interior surface 32 of the rear housing portion 30 is rotationally symmetrical.

Figure 18:
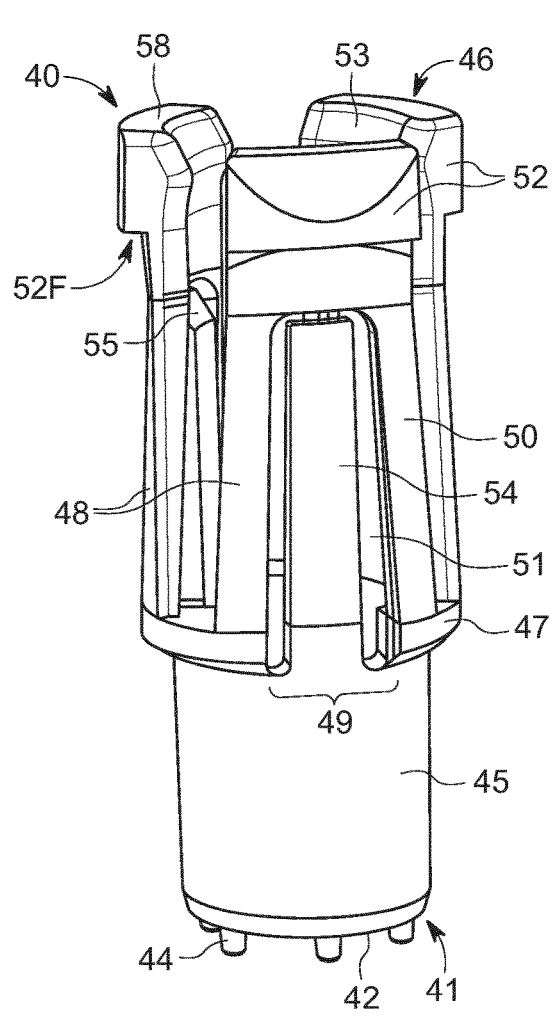
FIG. 18 is a perspective side view of the sleeve of the blood sampling device of FIG. 13 in a holding configuration.
Figure 19:
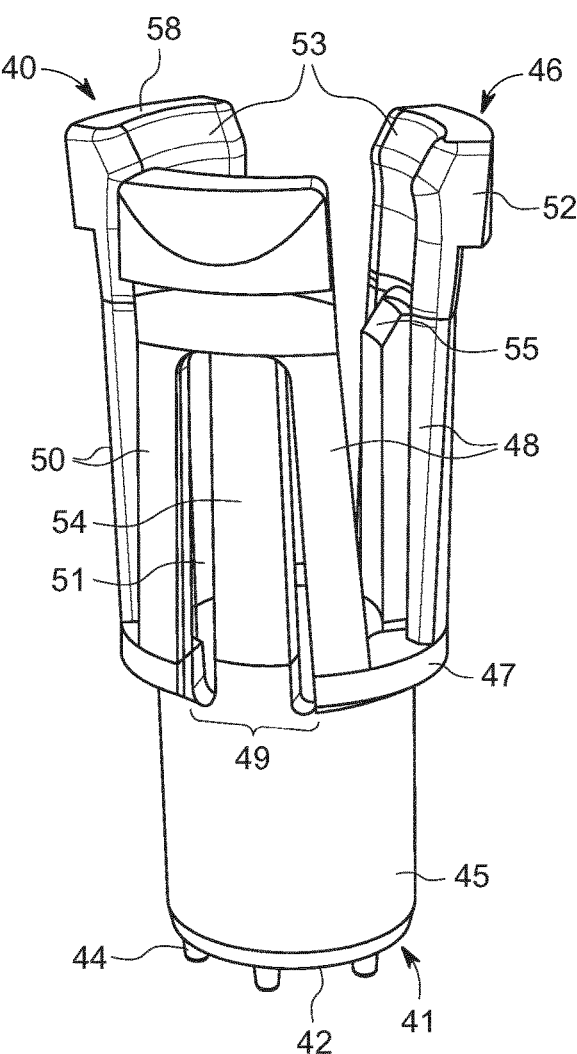
FIG. 19 is a perspective side view of the sleeve of the blood sampling device of FIG. 13 in a release configuration.

Referring to FIGS. 18 and 19, the sleeve 40 comprises a forward end 41 and a rearward end 46. The forward end 41 has a front face in the form of a flat base surface 42 defining a central aperture 43 through which the sharp tip 62 of the lancet 60 can project in use. The flat base surface also comprises a plurality of projections 44 arranged in an annular array around the central aperture 43. The projections 44 are designed to stimulate the skin so as to 'confuse' the nerve endings and alleviate the perceived pain experienced when the lancet tip penetrates the skin to make an incision.

The forward end 41 of the sleeve 40 also comprises a cylindrical tubular portion 45 extending rearwardly from the flat base surface to around one third of the length of the sleeve 40. At the rear end of the tubular portion 45 there is an annular seat 47 having the same internal diameter as the tubular portion 45 but a larger external diameter than the tubular portion 45 such that it projects radially outwardly from the rear end of the tubular portion 45. There are three equidistantly spaced gaps 49 in the annular seat 47.

Three holding arms 48 are equidistantly spaced around the annular seat 47 and extend rearwardly from the annular seat 47 for around two thirds of the length of the sleeve 40, i.e. to the rearward end 46 of the sleeve 40. Each holding arm 48 comprises two fingers 50 separated by a gap 51. Each gap 51 is aligned with a gap 49 in the annular seat 47. The two fingers 50 of each holding arm 48 are joined at a rearward end 58 of the respective holding arm 48 such that there is no gap between them, i.e. forming a joined rearward end 58. The joined rearward end 58 of each holding arm 48 comprises a flange 52 on its external surface which projects radially outwardly from the forwardly adjacent portion of the joined rearward end 58. The front surface 52F of the flange 52 is arranged at a 90° angle to the immediately forwardly adjacent portion of the joined rearward end 58.

The internal rear end surface of the joined rearward end 58 of each holding arm 48 is a sloped surface 53. Each holding arm 48 is biased outwardly such that it splays outwardly in its natural resting position as shown in FIG. 19. This is the release configuration of the sleeve 40. The three holding arms 48 are resiliently deformable. This means that they can be pressed inwardly towards each other into a holding configuration as shown in FIG. 18 and will return to their splayed release configuration as shown in FIG. 19 on removal of this inward pressure.

Three resiliently deformable blocking legs 54 extend rearwardly from the tubular cylindrical portion 45 of the sleeve 40. Each blocking leg 54 is located in a gap 49 in the annular seat 47 and the corresponding gap 51 in a holding arm 48, i.e. each blocking leg 54 is located between the two fingers 50 of a holding arm 48. In this embodiment, all of the blocking legs 54 are longitudinally aligned with the tubular portion 45 of the sleeve 40, i.e., none of the blocking legs 54 are splayed outwardly. This means that when the sleeve 40 is in its natural resting position shown in FIG. 19, the rearward end of each blocking leg 54 is positioned radially inwardly relative to the rearward end of each holding arm 48. The rearward end of each blocking leg 54 has a chamfered surface in the form of abutment surface 55 on the inner rear edge thereof.

Referring to FIGS. 21(*b*) to 21(*e*), the inner surface 57 of the tubular portion 45 of the sleeve 40 comprises a portion of reduced diameter 59a which extends rearwardly from the flat base surface and an immediately adjacent portion of increased diameter 59b which extends rearwardly to the annular seat 47. The join between this portion of reduced diameter 59a and the immediately adjacent portion of increased diameter 59b forms an abutment surface 56 on the inner surface 57 of the sleeve 40.

Figure 20:
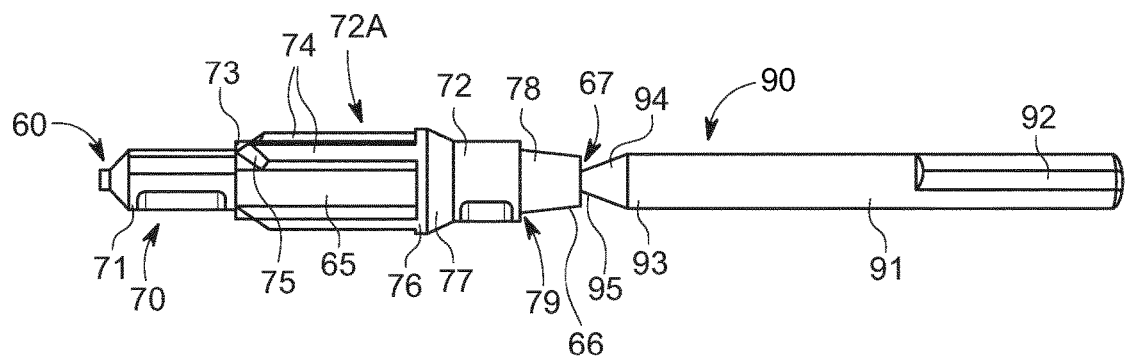
FIG. 20 is a side view of the lancet and safety cap of the blood sampling device of FIG. 13.

Referring to FIG. 20, the lancet 60 comprises a lancet body 65 moulded around a needle 61. The lancet body 65 has a forward end 66 and a rearward end 70. The rearward end 70 comprises a substantially cylindrical tail 71 shaped and dimensioned such that the urging member 80 can fit over it. Immediately forward of the cylindrical tail 71 is a substantially cylindrical main body portion 72 which has a larger diameter than the cylindrical tail 71. As such, the rear end of the main body portion 72 provides a rear seat 73 at the front of the cylindrical tail 71. The rear seat 73 has a larger diameter than the urging member 80 such that when the blood sampling device 1 is in an initial assembled configuration, the urging member 80 abuts the rear seat 73.

The main body portion 72 has eight elongate ribs (i.e. splines) 74 equidistantly spaced around its circumference, defining a splined portion 72A. Each elongate rib 74 extends axially from the rear end of the main body portion 72 to around two thirds of the length of the main body portion 72. The rearward end of each elongate rib 74 has a sloped helical guiding surface 75. The forward end of each elongate rib 74 merges with a circumferential protrusion 76 which projects radially outwardly on the main body portion 72. The circumferential protrusion 76 has a chamfered front face in the form of sloped surface 77. The outer surface of the main body portion 72 is rotationally symmetrical. This does not include non-functioning features such as indentations on the outer surface of the main body portion 72 which are requirements of the manufacturing process.

The forward end 66 of the lancet body 65 has a frustoconical portion 78 having a planar front surface 67. The sharp tip 62 of the needle 61 projects from the front surface 67 of the lancet body 65. The front end of the frustoconical portion 78 has a smaller diameter than the rear end. The rear end of the frustoconical portion 78 has a smaller diameter than the front end of the main body portion 72 such that a front seat 79 is formed by the front end of the main body portion 72 between the circumferential edge of the main body portion 72 and the circumferential edge of the rear end of the frustoconical portion 78.

An elongate safety cap 90 is integrally moulded with the front surface 67 of the lancet body 65 such that the sharp tip 62 of the lancet needle 61 is initially concealed within the safety cap 90. The safety cap 90 comprises a graspable portion 91 which is external to the housing 10 when the blood sampling device 1 is assembled and a stem 93 which is substantially located within the housing 10 when the blood sampling device 1 is assembled. The stem 93 has a frustoconical rearward end 94 which forms a frangible connection 95 with the front surface 67 of the lancet body 65. The graspable portion 91 comprises diametrically opposed axially extending detents 92 which act as gripping surfaces for the user.

Assembly of the blood sampling device 1 will now be described. Importantly, none of the components of the blood sampling device 1 require manual rotational alignment during assembly, improving the ease of manufacture. In addition, none of the components require manual connection, each can simply be inserted into the housing. It is noted that the assembly of the blood sampling devices 1 may be fully automated (i.e. no manual assembly) and in large numbers. With regards to equipment, having free orientation on assembly (i.e. it does not matter what rotational orientation the components are assembled in) saves a significant amount of time, thus reducing cost. Furthermore, having free orientation on assembly removes one of the considerable causes of assembly failure, namely the incorrect orientation of assembly components. The below assembly process will be described as a manual process for simplicity but the same principles of orientation free assembly apply equally to an automated assembly process.

FIG. 21(*a*) shows the blood sampling device 1 in an initial assembled configuration. To assemble the blood sampling device 1, the front housing portion 15 is held with its forward end 16 facing downwards and its open rearward end 17 facing upwards. The sleeve 40 is inserted into the front housing portion 15 via the open rear end 17 such that the forward end 41 of the sleeve 40 projects through the circular aperture 18 in the forward end 16 of the front housing portion 15. The annular seat 47 of the sleeve 40 abuts the inner surface 22 of the forward end 16 of the front housing portion 15 which prevents further forward movement of the sleeve 40. The inner surface 22 of the front housing portion 15 has a larger diameter than the tubular cylindrical portion 45 of the sleeve 40 but a smaller diameter than the holding arms 48 when they are in their splayed resting position (FIG. 19). As such, insertion of the sleeve 40 into the front housing portion 15 forces the holding arms 48 radially inwardly so that the sleeve 40 is in the holding configuration (FIGS. 18 and 22(*a*)). The rotational orientation of the sleeve 40 relative to the front housing portion 15 does not matter as the inner surface 22 of the front housing portion 15 is rotationally symmetrical.

The lancet 60 and frangibly connected safety cap 90 are then inserted into the front housing portion 15 via the open rear end 17, safety cap 90 first. The diameter of the safety cap 90 is smaller than the diameter of the central aperture 43 in the flat base surface of the sleeve 40 so that it passes through the central aperture 43 on insertion. The diameter of the forward end 66 of the lancet body 65 is smaller than the internal diameter of the rear end 46 of the sleeve 40, i.e. the distance between the rear ends of the holding arms 48. Therefore, the forward end 66 of the lancet body 65 passes through the rear ends of the holding arms 48 on insertion. However, the diameter of the circumferential protrusion 76 having a sloped surface 77 is larger than the diameter of the rear end 46 of the sleeve 40 when the sleeve 40 is in the holding configuration. As such, when the sloped surface 77 contacts the sloped surface 53 on the internal surfaces of the rear end of the holding arms 48, further forward movement of the lancet 60 is prevented, i.e. movement of the sloped surface 77 past the sloped surfaces 53 on the holding arms 48 is prevented. The rotational orientation of the lancet 60 and frangibly connected safety cap 90 relative to the front housing portion 15 and the sleeve 40 does not matter.

The compression spring 80 is then placed on the cylindrical tail 71 of the lancet body 65. As above, the inner diameter of the compression spring 80 is larger than the diameter of the cylindrical tail 71 of the lancet body 65 so the forward end 81 of the compression spring 80 passes over the cylindrical tail 71 until it comes to rest against the rear seat 73. The rear seat 73 has a larger diameter than the compression spring 80 so the compression spring 80 is prevented from moving forward past it. The rotational orientation of the compression spring 80 does not matter.

The rear housing portion 30 is then placed over the rearward end 70 of the lancet body 65, the compression spring 80 and the rearward end 17 of the front housing portion 15. The rotational orientation of the rear housing portion 30 relative to the other components does not matter i.e. the rear housing portion 30 can be placed on the rear end of the device 1 in any orientation. If the elongate ribs 37 on the interior surface 32 of the rear housing portion 30 are not rotationally aligned with the elongate ribs 74 on the outer surface of the lancet body 65, the helical guiding surfaces 38 of the elongate ribs 37 on the interior surface 32 of the rear housing portion 30 will contact the helical guiding surfaces 75 of the elongate ribs 74 on the outer surface of the lancet body 65 so that the rear housing portion 30 self-aligns with the lancet body 65, i.e. no manual rotation is required. Each of the elongate ribs 37 on the interior surface 32 of the rear housing portion 30 is guided in between two elongate ribs 74 on the outer surface of the lancet body 65 and vice versa. Therefore, the rear housing portion 30 and the lancet 60 cannot rotate relative to each other when assembled. It is noted that instead of providing elongate ribs on each of the rear housing portion 30 and the lancet body 65, one of the components could be provided with splines having guiding surfaces (such as the helical guiding surfaces of this embodiment) and the other could be provided with a single protrusion. Other alternative arrangements would be apparent to the skilled person.

The rear housing portion 30 is pushed forwardly until the three equidistantly spaced radial protrusions 33 on the interior surface 32 of the rear housing portion 30 are positioned in the circumferential detent 20 on the outer surface 21 of the front housing portion 15. The three radial protrusions 33 form a snap fit in the circumferential detent 20, securing the front housing portion 15 and the rear housing portion 30 together. The rearward end 17 of the front housing portion 15 is located within the open forward end 31 of the rear housing portion 30 to form a portion of the passage 11 having a reduced diameter in the portion of overlap. The rear housing portion 30 is prevented from moving further forward when pushed by abutment of the open forward end 31 of the rear housing portion 30 with the seat 23 formed by the rear end of the bulbous head 19 of the front housing portion 15.

As such, in the initial assembled configuration, the front housing portion 15 and the rear housing portion 30 form a housing 10 having a forward end 12 and a rearward end 13. The housing 10 has an aperture 18 in said forward end 12 and the inner surface 22 of the front housing portion 15 and the interior surface 32 of the rear housing portion together form an interior surface of the housing 10 defining a passage 11. The passage 11 is narrower in the forward end 12 of the housing 10 because the front housing portion 15 is located inside the rear housing portion 30. The compression spring 80, the lancet 60, the stem 93 of the safety cap 90 and the rearward end 46 of the sleeve 40 are located in the passage 11 in the initial assembled configuration. The forward end 41 of the sleeve 40 and the graspable portion 91 of the safety cap 90 project through the aperture 18 in the forward end 16 of the housing 10, i.e. they are not located in the passage 11 in the initial assembled configuration.

The components of the blood sampling device 1 could be assembled in a different order so long as the arrangement of components in the blood sampling device 1 is the same after assembly. For example, the compression spring 80 and lancet 60 with frangibly connected safety cap 90 could be inserted into the rear housing portion 30 before inserting the sub-assembled sleeve 40 and the front housing portion 15.

Figure 21C:
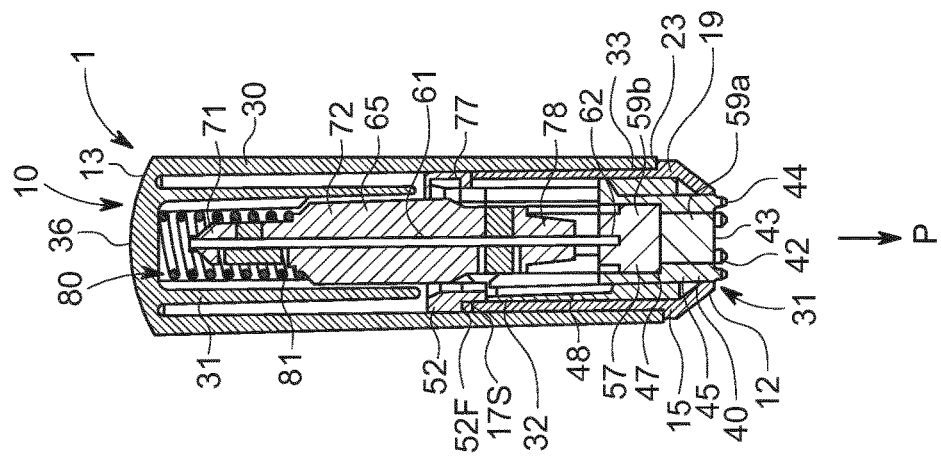
FIG. 21(c) is a side sectional view of the blood sampling device of FIG. 13 in a firing configuration.
Figure 21B:
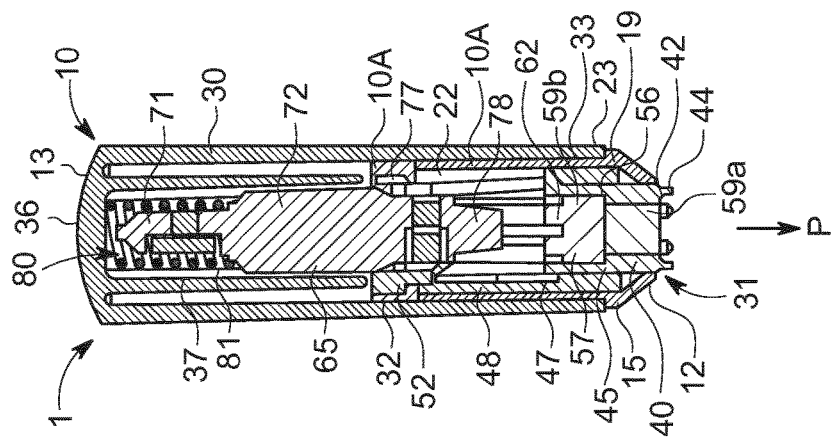
FIG. 21(b) is a side sectional view of the blood sampling device of FIG. 13 in a pre-release configuration.
Figure 21A:
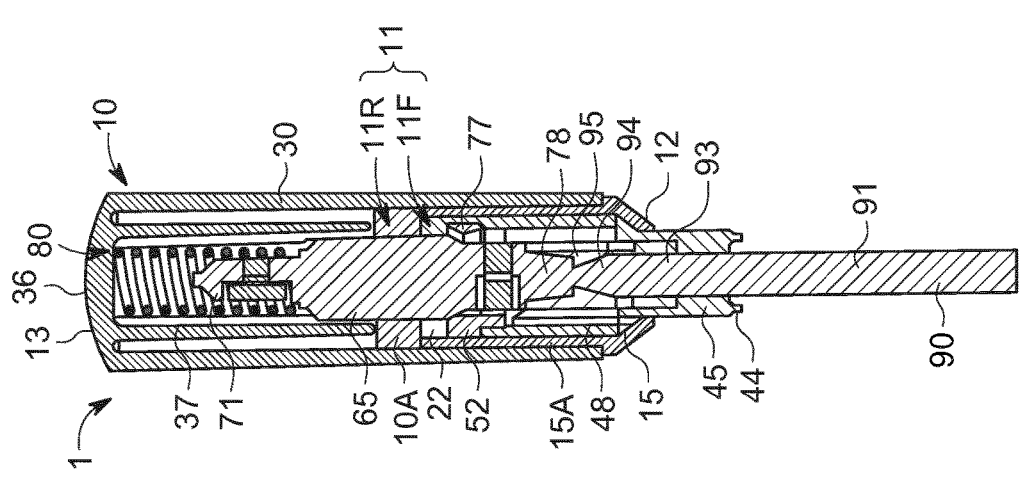
FIG. 21(a) is a side sectional view of the blood sampling device of FIG. 13 in an initial assembled configuration.

Referring to FIGS. 21(a)-(e) and 22(a)-(d), operation of the blood sampling device 1 will now be described. Referring to FIG. 21(a), when the blood sampling device 1 is in the initial assembled configuration, the first step to be taken by the user is removal of the safety cap 90. The safety cap 90 may be removed by holding the graspable portion 91 and twisting it relative to the housing 10 about the direction of pricking P. As each of the elongate ribs 37 on the interior surface 32 of the rear housing portion 30 is located between two elongate ribs 74 on the outer surface of the lancet body 65 and vice versa, the lancet body 65 cannot rotate relative to the housing 10. As such, the twisting action of the graspable portion 91 rotates the safety cap 90 relative to the housing 10 and the lancet body 65. This breaks the frangible connection 95 between the safety cap 90 and the lancet 60 such that the safety cap 90 can be removed from the housing 10. Withdrawal of the safety cap 90 in the pricking direction P exposes the sharp tip 62 of the needle 61 inside the housing 10. Thus, until this time the needle 61 is hermetically sealed prior to use. The blood sampling device is in a pre-primed position (not shown) in which the sharp tip 62 is located in the housing (within the passage 11) and the compression spring 80 is not yet primed. Abutment of the sloped surface 77 on the lancet body 65 with the sloped surfaces 53 on the internal surfaces of the holding arms 48 prevents the lancet 60 from moving forwardly in the passage 11 because the sleeve 40 is in the holding configuration, i.e. movement of the sloped surface 77 past the sloped surfaces 53 is prevented. Abutment of the annular seat 47 of the sleeve 40 against the inner surface 22 of the forward end 16 of the front housing portion 15 prevents forward movement of the sleeve 40 in the passage 11. Thus, the blood sampling device 1 is held in the pre-primed position until actuated by the user.

To operate the blood sampling device 1, the user holds the housing 10 and places the flat base surface of the sleeve 40 (which is the forwardmost part of the blood sampling device 1 in the pre-primed position) against the surface of the skin from which blood is to be sampled. The annular array of projections 44 therefore contact the skin of the user, stimulating the skin so as to 'confuse' the nerve endings and alleviate the perceived pain experienced when the lancet tip penetrates the skin to make an incision. To actuate the blood sampling device 1, the user presses the housing 10 towards the skin. This causes the housing 10 to move forwardly relative to the sleeve 40 as the sleeve 40 is held against the surface of the skin, i.e. the sleeve 40 moves rearwardly in the passage 11.

Passage 11 comprises a rearward portion 11R and a forward portion 11F immediately adjacent rearward portion 11R, forward portion 11F having a smaller diameter than rearward portion 11R. Holding arms 48 are located in passage forward portion 11F when sleeve 40 is in the holding configuration such that they are urged radially inwards, and rearward movement of sleeve 40 in passage 11 to passage rearward portion 11R results in holding arms 48 moving radially outwards such that sleeve 40 is in the release position. In certain embodiments this movement of holding arms 48 is as a result of them moving to their relaxed position. In other embodiments, this movement is as a result of sloped surface 77 of lancet body 65 (which abuts sloped surface 53 of holding arms 48) deflecting holding arms 48 radially outwards. Front housing portion 15 comprises an inner portion 15A which is located inside rear housing portion 30 to form forward portion 11F of passage 11.

Figure 22B:
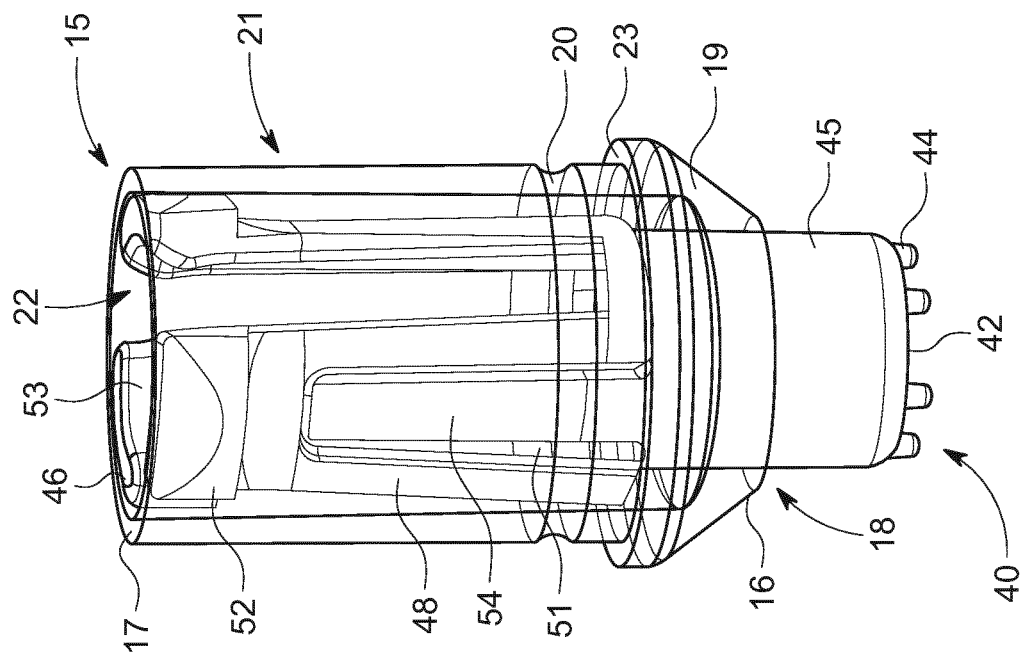
FIG. 22(b) is a part-transparent side view of the sleeve and front housing portion of the blood sampling device of FIG. 13 in a holding configuration.
Figure 22A:
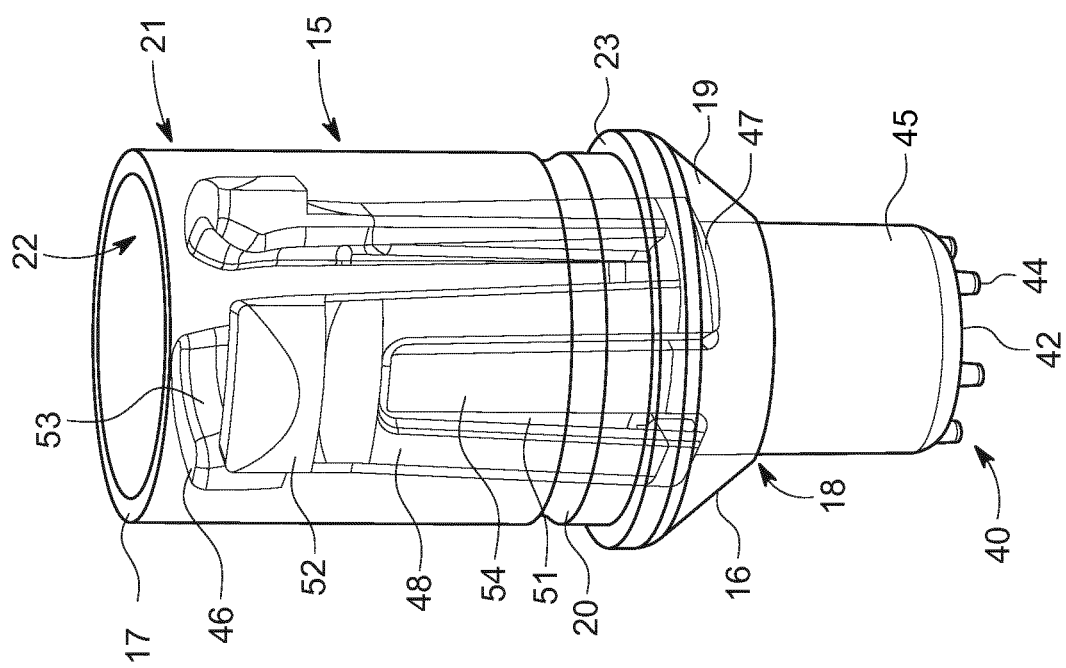
FIG. 22(a) is a part-transparent side view of the sleeve and front housing portion of the blood sampling device of FIG. 13 in an initial assembled configuration.

Referring to FIG. 22(b), the holding arms 48 are held inwardly by the front housing portion 15 during this initial rearward movement of the sleeve 40 in the passage 11 so the sleeve 40 is maintained in the holding configuration. As such, the sloped surface 77 on the lancet body 65 continues to abut the sloped surfaces 53 on the internal surfaces of the holding arms 48, preventing movement of the sloped surface 77 past the sloped surfaces 53 and thus forward movement of the lancet 60 relative to the sleeve 40. As such, the lancet 60 also moves rearwardly in the passage 11 with the sleeve 40 from the pre-primed position to a primed position. This compresses the compression spring 80 between the rear seat 73 formed by the main body portion 72 of the lancet body 65 and the rearward end of the passage 11 formed by the rear housing portion 30. The blood sampling device 1 is now in the pre-release configuration shown in FIG. 21(b) and the lancet 60 is in a primed position. The sharp tip 62 is located in the housing 10 (within the passage 11) in the primed position and the compression spring 80 is now primed i.e. it is compressed from its resting position.

If the user continues to push the blood sampling device 1 towards the skin, the sleeve 40 will continue to move rearwardly in the passage 11. Referring to FIG. 22(c), the holding arms 48 try to splay outwardly as the flange 52 of each holding arm 48 moves rearwardly past the rearward end 17 of the front housing portion 15. This is because the diameter of the passage 11 is larger behind the front housing portion 15. The compression spring 80 is also urging against the rear seat 73 formed by the main body portion 72 of the lancet body 65 which urges the lancet body 65 forwardly. As such, the sloped surface 77 on the lancet body 65 urges against the sloped surfaces 53 on the internal surfaces of the holding arms 48, forcing the holding arms 48 apart. However, as the front surface 52F of each flange 52 is not yet rearward of the rearward end 17 of the front housing portion 15, the holding arms 48 are still held inwardly by the front housing portion 15 and the sleeve 40 is still in the holding configuration. The lancet 60 is still in a primed position because it cannot yet travel forwardly past the holding arms 48. The sharp tip 62 is located in the housing 10 (within the passage 11) in the primed position and the compression spring 80 is primed i.e. it is compressed from its resting position.

Figure 22D:
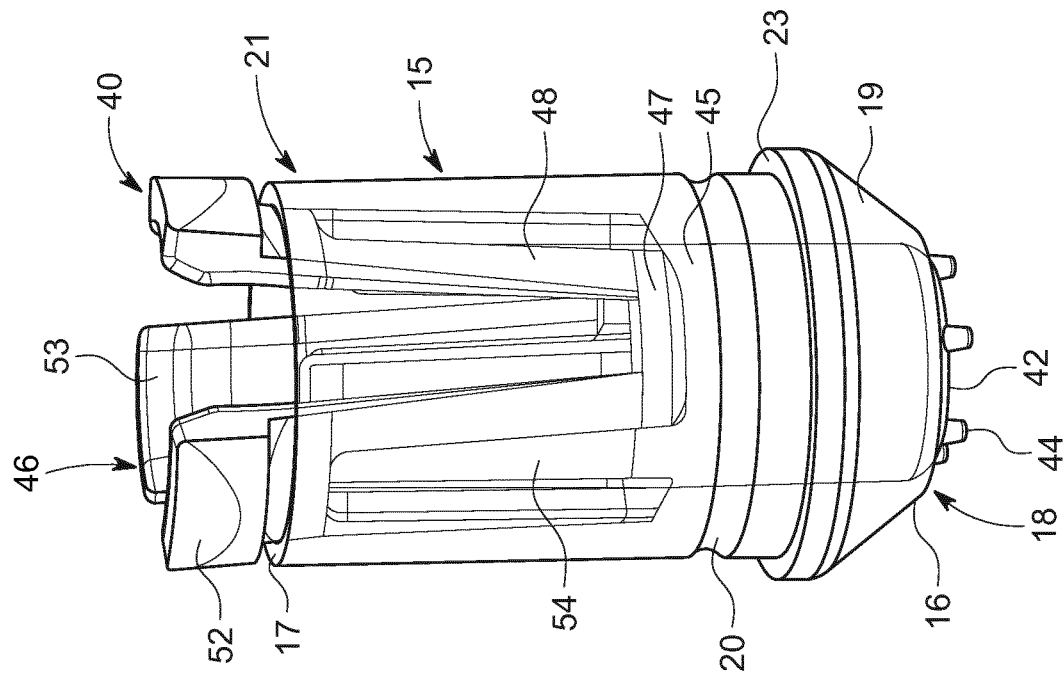
FIG. 22(d) is a part-transparent side view of the sleeve and front housing portion of the blood sampling device of FIG. 13 in a release configuration.
Figure 22C:
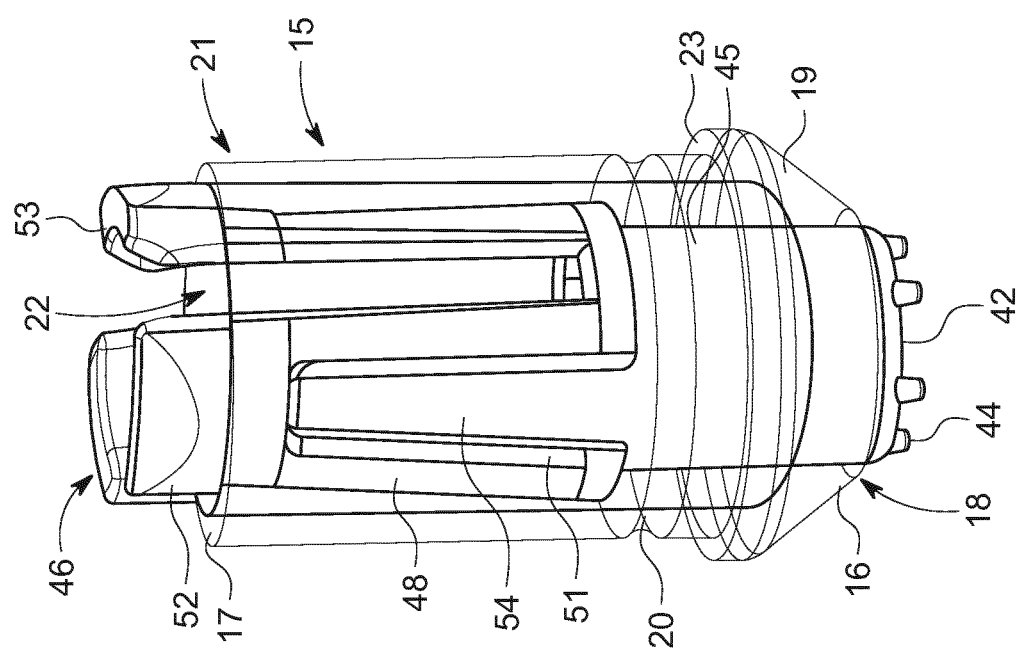
FIG. 22(c) is a part-transparent side view of the sleeve and front housing portion of the blood sampling device of FIG. 13 in a holding configuration.

Referring to FIG. 22(d), when the sleeve 40 moves sufficiently rearwardly in the passage 11, the flange 52 of each holding arm 48 is rearward of the rearward end 17 of the front housing portion 15. The three holding arms 48 splay outwardly under their own resilient bias and under the urging force of sloped surface 77 on the lancet body 65 against the sloped surfaces 53 on the internal surfaces of the holding arms 48. The blood sampling device 1 is in the firing configuration shown in FIG. 21(c) and the sleeve 40 is in the release configuration. This movement of the sleeve 40 from the holding configuration to the release configuration is very quick due to the sharp 90° angle between the front surface 52F of each flange 52 and the rearward end 17 of the front housing portion 15. As such, the three holding arms 48 spring outward into the release configuration as soon as the front surface 52F of each flange 52 is rearward of the rearward end 17 of the front housing portion 15, i.e. the front surface 52F of each flange 52 acts as a release point. The diameter of the circumferential protrusion 76 of the lancet body 65 is smaller than the internal diameter of the rear end 46 of the sleeve 40 when it is in the release configuration, i.e. the diameter of the circumferential protrusion 76 of the lancet body 65 is smaller than the distance between the rear ends of the holding arms 48. As such, the circumferential protrusion 76 and thus the sloped surface 77 of the lancet body 65 can move forwardly in the passage 11 past the sloped surfaces 53 and the lancet 60 fires forwardly under the force of the compression spring 80.

As the lancet 60 moves forwardly in the passage 11, the sloped surface 77 of the lancet body 65 contacts the abutment surfaces 55 on the inner rearward edge of each of the three blocking legs 54. The lancet 60 cannot push the sleeve 40 forwardly in the passage 11 because the forward surface (stop surface) 52F of the flange 52 on each of the holding arms 48 abuts stop surface 17S of the rearward end 17 of the front housing portion 15, preventing forward movement of the sleeve 40, i.e. the stop surface 17S of the rearward end 17 and the forward surface (stop surfaces) 52F act as cooperating latching surfaces. The sleeve 40 is also held in position by the user holding the blood sampling device 1 against the skin. As lancing is near instantaneous, upon reaching the release point, it would not be possible for the user to release pressure before firing of the blood sampling device 1 is finished. However, the force of the compression spring 80 is sufficient for the lancet body 65 splay the three blocking legs 54 outwardly by urging the sloped surface 77 on the lancet body 65 firstly past the abutment surfaces 55 on the inner rearward edge of each of the three blocking legs 54 and then the inside face of the blocking leg 54. However, the force of the compression spring 80 is sufficient for the lancet body 65 to splay the three blocking legs 54 outwardly by urging the sloped surface 77 on the lancet body 65 firstly past the abutment surfaces 55 on the inner rearward edge of each of the three blocking legs 54 and then past the inside face of each of the blocking leg 54.

Figure 21D:
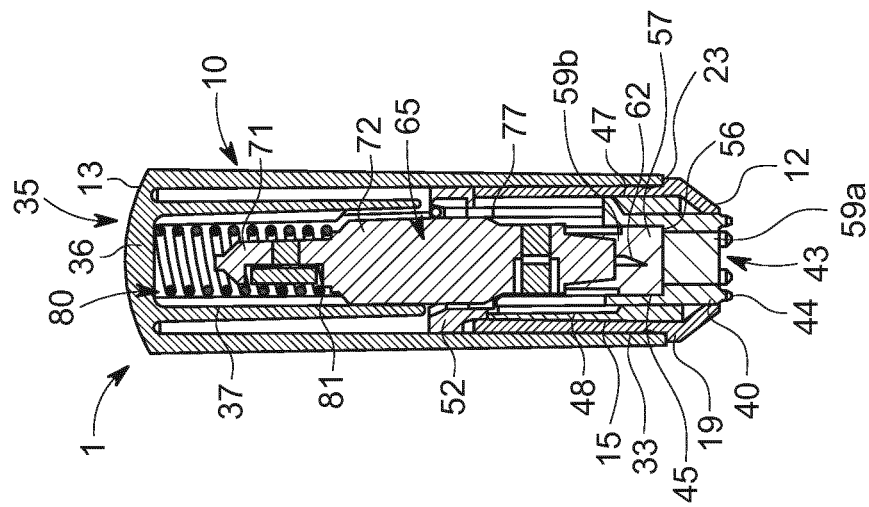
FIG. 21(d) is a side sectional view of the blood sampling device of FIG. 13 in a lancing configuration.

The lancet 60 continues to move forwardly in the passage 11 until the front seat 79 formed by the main body portion 72 of the lancet 60 abuts the abutment surface 56 on the inner surface 57 of the sleeve 40. This is the lancing configuration of the blood sampling device 1 in which the lancet 60 is in a lancing position. Referring to FIG. 21(d), the sharp tip 62 of the needle 61 projects through the central aperture 43 in the flat base surface of the sleeve 40 and thus also through the aperture 18 in the forward end 16 of the housing 10, to puncture the skin of the user, drawing a sample of blood from the user. The impact of the seat 79 on the abutment surface provides the same effect as described above in relation to Embodiment 1.

Figure 21E:
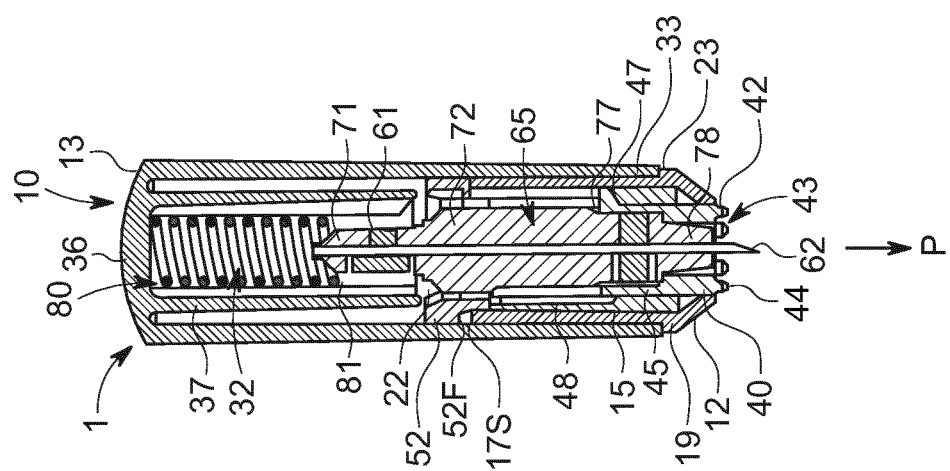
FIG. 21(e) is a side sectional view of the blood sampling device of FIG. 13 in a safe position after firing.

Referring to FIG. 21(e), the front seat 79 formed by the main body portion 72 of the lancet 60 strikes the abutment surface 56 on the inner surface 57 of the sleeve 40 with sufficient force to rebound. The lancet 60 therefore travels rearwardly in the passage 11 to retract the sharp tip 62 of the needle 61 into the housing 10. This rearward movement is assisted by the blocking legs 54 returning from their outwardly splayed position to their normal position parallel to the needle axis.

This ensures that the sloped surface 77 on the lancet body 65 moves rearwardly past the abutment surfaces 55 on the rear end of the blocking legs 54. When the front seat 79 formed by the main body portion 72 of the lancet 60 strikes the abutment surface 56 on the inner surface 57 of the sleeve 40 a significant amount of energy is lost. Therefore, there is not enough energy in the lancet 60 to re-compress the compression spring 80. The compression spring 80 therefore does not re-fire the lancet 60 forwardly in the passage 11 and the lancet 60 does not move forwardly with sufficient force to re-splay the blocking legs 54 and travel forwardly in the passage again. Thus, re-firing of the blood sampling device 1 is prevented and the lancet 60 is held sufficiently rearwardly from the aperture 18 in the forward end 16 of the housing 15, such that the sharp tip 62 is safe. Thus, the risk of the user accidentally pricking themselves with the used lancet is significantly reduced. As discussed above, the sleeve 40 cannot move forwardly in the passage 11 because the forward surface (stop surface) 52F of the flanges 52 on each of the holding arms 48 abuts the rearward end 17 of the front housing portion 15, preventing forward movement of the sleeve 40. Therefore, the device cannot be reused.

It will be apparent to a person skilled in the art that modifications and variations can be made to the described embodiment without departing from the scope of the invention as defined by the appended claims. Any incorporation of reference signs in the claims is solely to ease their understanding, and does not limit the scope of the claims.

The invention claimed is:

1. A lancing device comprising:
    a housing having a forward end and a rearward end, the housing defining a passage having an aperture in the forward end;
    a lancet comprising:
        a lancet body,
        a lancet tip supported at a forward end of the lancet body so as to project from the lancet body, and
        an impact surface defined in the forward end of the lancet body at a first predetermined distance from the lancet tip;
        wherein the lancet is mounted in the passage so as to be axially moveable with respect to the housing between a first position in which the lancet tip is positioned within the housing, and a second position in which the lancet tip extends through the aperture and beyond the forward end of the housing;
    an urging member which engages the lancet at least when the lancet is in the first position, and which can be energised to urge the lancet from the first position to the second position; and
    a sleeve movably located within the housing and around the forward end of the lancet body, wherein the sleeve has a front portion that that projects a first distance through the aperture in the housing in a first sleeve position and defines an opening through which the lancet tip can project, wherein the front portion has
        a front surface,
        a holding structure that can be moved into and out of engagement with the lancet body, and
        an internal stop surface located at a second predetermined distance from the front surface, wherein the internal stop surface is arranged to be engaged by the impact surface of the lancet body when in the second position, wherein the second predetermined distance is smaller than the first predetermined distance;
        wherein movement of the sleeve rearward into the housing from a first sleeve position to a second sleeve position when the lancet body is engaged with the holding structure moves the lancet body to the first position and energises the urging member, and wherein in use, the energised urging member can move the lancet body from the first position towards the second position to cause the lancet tip to project through the opening in the sleeve by a predetermined amount before the impact surface on the lancet body engages the internal stop surface of the sleeve.

2. A lancing device as claimed in claim 1, wherein moving the holding structures out of engagement with the lancet body releases the lancet body to move to the second position under the influence of the urging member.

3. A method of operating a lancing device as claimed in claim 2, comprising:
   with the sleeve in the first sleeve position and the holding structure engaged with the lancet body, placing the front surface of the sleeve in contact with a skin surface;
   urging the housing towards the skin surface to move the sleeve rearward towards a second sleeve position and move the lancet body to the first position and energise the urging member; and
   moving the holding structures out of engagement with the lancet body to release the lancet body to move to the second position under the influence of the urging member.

4. A lancing device as claimed in claim 1, wherein the diameter of the housing is smaller at the forward end than at the rearward end.

5. A lancing device as claimed in claim 4, wherein the holding structures comprise outwardly-biased resilient legs that are held in engagement with the lancet body by the inner wall of the forward end of the housing when in the first sleeve position, and are released from engagement with the lancet body when the sleeve is moved to the second sleeve position.

6. A lancing device as claimed in claim 5, wherein the engaged parts of the outwardly-biased resilient legs and lancet body comprise complementary sloped surfaces.

7. A lancing device as claimed in claim 5, wherein the outwardly-biased resilient legs comprise locking members that engage in the housing to hold the sleeve in the second sleeve position.

8. A lancing device as claimed in claim 5, wherein the outwardly-biased resilient legs further comprise retaining structures, wherein the retaining structures are positioned such that they will engage formations on the lancet body after recoil from the impact surface and hold it in the housing so that the lancet tip is within the housing.

9. A lancing device as claimed in claim 8, wherein the retaining structures comprise inwardly biased legs.

10. A lancing device as claimed in claim 9, wherein each leg comprises an abutment surface and the lancet body comprises a cooperating abutment surface, wherein the lancet body abutment surface abuts the leg abutment surface to prevent forward movement of the lancet in the passage.

11. A lancing device as claimed in claim 10, wherein the lancet body cooperating abutment surface is located rearwardly of the leg abutment surface when the lancet body is in the first position and wherein forward movement of the lancet body from the first position to the second position splays the leg outwardly such that the lancet body abutment surface can move past the leg abutment surface.

12. A lancing device as claimed in claim 1, wherein the sleeve further comprises retaining structures, wherein the retaining structures are positioned such that they will engage formations on the lancet body after recoil from the impact surface and hold it in the housing so that the lancet tip is within the housing.

13. A lancing device according to claim 1, wherein the front surface of the sleeve comprises a skin contacting front surface including a flat base surface and a plurality of projections extending from the flat base surface.

* * * * *